United States Patent [19]

Chan

[11] Patent Number: 5,609,158
[45] Date of Patent: Mar. 11, 1997

[54] APPARATUS AND METHOD FOR PREDICTING CARDIAC ARRHYTHMIA BY DETECTION OF MICROPOTENTIALS AND ANALYSIS OF ALL ECG SEGMENTS AND INTERVALS

[75] Inventor: Eric K. Y. Chan, Austin, Tex.

[73] Assignee: Arrhythmia Research Technology, Inc., Austin, Tex.

[21] Appl. No.: 431,992

[22] Filed: May 1, 1995

[51] Int. Cl.$^6$ ............................................. A61B 5/0468
[52] U.S. Cl. ........................................................ 128/705
[58] Field of Search ........................ 128/696, 702–705; 364/413.05, 413.06

[56] References Cited

U.S. PATENT DOCUMENTS

| | | | |
|---|---|---|---|
| 3,884,221 | 5/1975 | Eastman . | |
| 4,422,459 | 12/1983 | Simson | 128/702 |
| 4,458,692 | 7/1984 | Simson | 128/705 |
| 4,492,235 | 1/1985 | Sitrick | 128/705 |
| 4,592,367 | 6/1986 | Imran | 128/706 |
| 4,616,659 | 10/1986 | Prezas et al. | 128/706 |
| 4,630,204 | 12/1986 | Mortara | 364/417 |
| 4,679,144 | 7/1987 | Cox et al. | 364/417 |
| 4,680,708 | 7/1987 | Ambos et al. | 364/417 |
| 4,704,681 | 11/1987 | Shimizu et al. | 364/417 |
| 4,732,158 | 3/1988 | Sadeh | 128/702 |
| 4,742,458 | 5/1988 | Nathans et al. | 364/417 |
| 4,802,491 | 2/1989 | Cohen et al. | 128/702 |
| 4,924,875 | 5/1990 | Chamoun | 128/696 |
| 4,947,857 | 8/1990 | Albert et al. | 128/696 |
| 4,961,428 | 10/1990 | Nikias et al. | 128/699 |
| 5,046,504 | 9/1991 | Albert et al. | 364/413.06 |
| 5,092,341 | 3/1992 | Kelen | 128/702 |
| 5,109,862 | 5/1992 | Kelen et al. | 128/702 |
| 5,199,438 | 4/1993 | Pearlman | 128/670 |
| 5,211,179 | 5/1993 | Haberl et al. | 128/702 |
| 5,215,099 | 6/1993 | Haberl et al. | 128/702 |
| 5,271,411 | 12/1993 | Ripley et al. | 128/702 |

FOREIGN PATENT DOCUMENTS 0155670  9/1985  European Pat. Off. .

OTHER PUBLICATIONS

Berbari et al., "A computerized Technique to Record New Components of the Electrocardiogram", IEEE Proceedings vol. 65, No. 5 (May 1977) pp. 799–802.

"First Derivative of the Electrocardiogram," by Paul H. Langner, Jr., M.D., F.A.C.P., and David B. Geselowitz, Ph.D., taken from *Circulation Research*, vol. X, pp. 220–226 (Feb., 1962).

(List continued on next page.)

*Primary Examiner*—Jeffrey R. Jastrzab
*Attorney, Agent, or Firm*—Fitch, Even, Tabin & Flannery

[57] ABSTRACT

An apparatus and method for the acquisition and analysis of electrocardiogram signals, to non-invasively detect and quantify presence of abnormal cardiac conduction patterns in patients at risk of heart disease, e.g. ventricular tachycardia; atrial fibrillation and flutter. Signals from the orthogonal X, Y and Z surface leads are amplified, digitized and either stored for later processing, or processed immediately. The incoming beats can either be R wave-triggered, aligned and ensemble-averaged for studies of patients at risk for ventricular pathologies such as ventricular tachycardia, or P wave-triggered, aligned and ensemble-averaged for studies of patients at risk for atrial pathologies, e.g. atrial fibrillation and flutter. QRS onset and offset, and P wave onset and offset, are calculated for ventricular and atrial post-analysis applications, respectively. The windowed Fourier transform of the second derivative (acceleration) of the signal-averaged ECG is calculated for particular regions of interest for each lead, including the intra-QRS, ST-segment, T and P wave regions. A novel Spectral Change Index, calculated from the resulting "acceleration spectrum" for each lead as well as the composite (X+Y+Z) lead, serves to quantify the degree of spectral "fragmentation" within a prespecified bandwidth. It thereby provides a quantitative index to help stratify patients at risk for potentially lethal cardiac (atrial and ventricular) pathologies.

27 Claims, 6 Drawing Sheets

OTHER PUBLICATIONS

"Localization of the Site of Myocardial Scarring in Man by High–Frequency Components," by Nancy C. Flowers, M.D., et al., taken from *Circulation*, vol. XL, pp. 927–934 (Dec., 1969).

"High–Frequency Components in the Electrocardiogram: A Comparative Study of Normals and Patients with Myocardial Disease," by Ernest W. Reynolds, Jr., M.D., et al., taken from *Circulation*, vol. XXXV, pp. 195–206 (Jan., 1967).

"Study of High Frequency Components in Electrocardiogram by Power Spectrum Analysis," by Ernst K. Franke, Dr. Ing., et al., taken from *Circulation Research* vol. X, pp. 870–879 (Jun., 1962).

"Spectral Estimation of the Electrocardiogram," by Edward J. Berbari, et al., taken from *Annals New York Academy of Science*, pp. 197–208 (1990).

"Computerized Measurement of the First Derivative of the QRS Complex: Theoretical and Practical Considerations," by Ary L. Goldberger and Valmik Bhargava, taken from *Computers and Biomedical Research*, vol. 14, pp. 464–471 (1981).

"Instantaneous Power Spectra," by Chester H. Page, taken from *Journal of Applied Physics*, vol. 23, No. 1, pp. 103–106 (Jan., 1952).

"Simulation of Nonstationary Spectral Analysis of Turbulance in the Aorta Using a Modified Autoregressive or Maximum Entropy (AR/ME) Method," by T. Yamaguchi, et al., taken from *Medical and Biological Engineering and Computing*, vol. 25, pp. 533–542 (Sep., 1987).

"Methods for Analyzing Cardiac Late Potentials," by Edward J. Berbari, Ph.D., et al., taken from *Computers in Cardiology*, pp. 35–40 (1987).

"A New Robust 2–D Spectral Estimation Method and its Application in Cardiac Data Analysis," by Chrysostomos L. Nikias, Ph.D., et al., taken from *ICASSP '82 Proceedings, IEEE International Conference on Acoustics, Speech and Signal Processing*, vol. 2, of 3, May 3, 4 and 5, 1982, Paris, France.

"Frequency Analysis of the ECG With Maximum Entropy Method (MEM) Versus Fast Fourier Transform (FFT) for Identification of Patients With Ventricular Tachycardia," by Ralph Haberl, et al., taken from *Circulation Supplement, Abstracts from the 60th Scientific Sessions, American Heart Associaton*, Part II, vol. 76, pp. 11–13, (Oct., 1987).

"Comparison of Frequency and Time Domain Analysis of the Signal–Averaged Electrocardiogram in Patients With Ventricular Tachycardia and Coronary Artery Disease: Methodologic Validation and Clinical Relevance," by Ralph Haberl, et al., taken from *JACC*, vol. 12, pp. 150–158 (Jul., 1988).

"Spectral Mapping of the Electrocardiogram With Fourier Transform for Identification of Patients With Sustained Ventricular Tachycardia and Coronary Artery Disease," by Ralph Haberl, et al., taken from *European Heart Journal*, vol. 10, pp. 316–322 (1989).

"Fast–Fourier Transform Analysis of Signal–Averaged Electrocardiograms for Identification of Patients Prone to Sustained Ventricular Tachycardia," by Michael E. Cain, M.D., et al., taken from *Diagnostic Methods–Electrophysiology*, vol. 69, No. 4, pp. 711–720 (Apr., 1984).

"Quantification of Differences in Frequency Contents of Signal–Averaged Electrocardiograms in Patients With Compared to Those Without Sustained Ventricular Tachycardia," by Michael E. Cain, M.D., et al., taken from *The American Journal of Cardiology*, vol. 55, pp. 1500–1505 (Jun., 1, 1985).

"System Identification Techniques for Adaptive Noise Cancelling", by Benjamin Friedlander, taken from *IEEE Transactions on Acoustics, Speech and Signal Processing* vol. ASSP–30, No. 5, pp. 699–709 (Oct., 1982).

"Fast Adaptive Least Squares Algorithms for Power Spectral Estimation," by Nicholas Kalouptsidis, et al., taken from *IEEE Transactions on Acoustics, Speech and Signal Processing*, vol. ASSP–35, No. 5, pp. 661–670 (May, 1987).

"A New Autoregressive Spectrum Analysis Algorithm," by Larry Marple, taken from *IEEE Transactions on Acoustics, Speech and Signal Processing*, vol. ASSP–28, No. 4, pp. 441–453 (Aug., 1980).

"Selecting the Order of Autoregressive Models from Small Samples," by Piet M. T. Broersen, taken from *IEEE Transactions on Acoustics, Speech and Signal Processing*, vol. ASSP–33, No. 4, pp. 874–879, (Aug., 1985).

"Statistical Predictor Identification," by Hirotugu Akaike, pp. 203–217 (Dec., 1969).

"Probability, Random Variables and Stochastic Processes–Spectral Estimation," by Anthanasios Paopoulis, taken from *Polytechnic Institute of New York*, Second Edition, pp. 496–498, (1984).

"The Anatomic Basis for High–Frequency Components in the Electrocardiogram," by Nancy F. Flowers, M.D., et al., taken from *Circulation*, vol. XXXIX, pp. 531–539 (Apr., 1969).

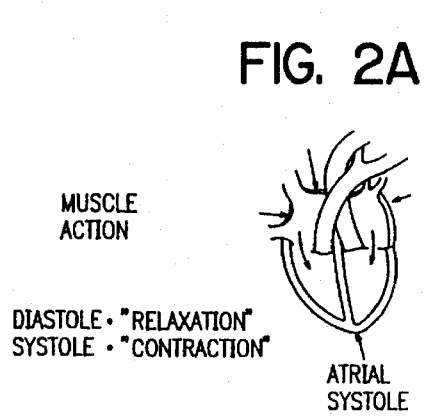
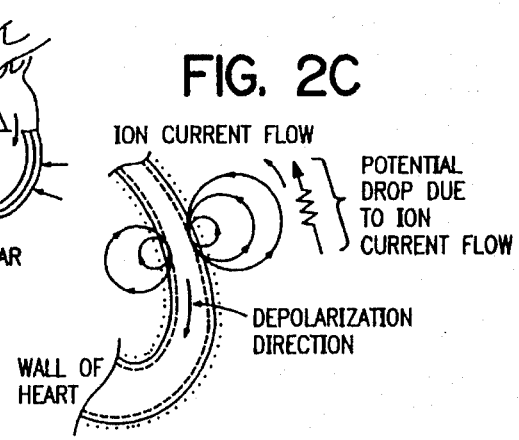

MUSCLE
ACTION

DIASTOLE - "RELAXATION"
SYSTOLE - "CONTRACTION"

VENTRICULAR
SYSTOLE

ATRIAL
SYSTOLE

ION CURRENT FLOW

POTENTIAL
DROP DUE
TO ION
CURRENT FLOW

DEPOLARIZATION
DIRECTION

WALL OF
HEART

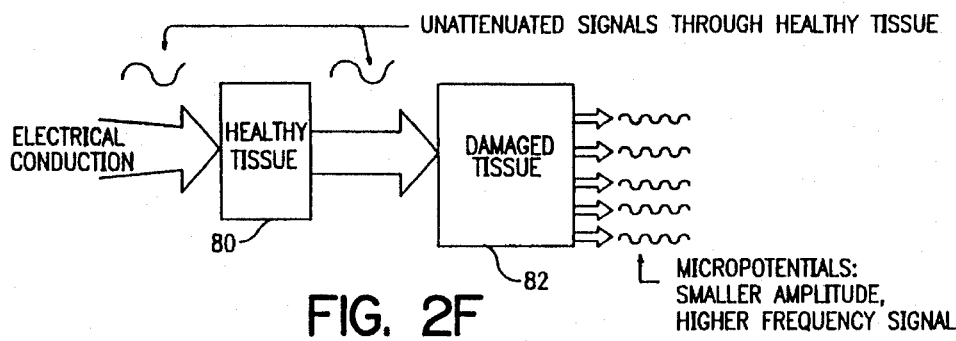

UNATTENUATED SIGNALS THROUGH HEALTHY TISSUE

ELECTRICAL
CONDUCTION

HEALTHY
TISSUE
80

DAMAGED
TISSUE
82

MICROPOTENTIALS:
SMALLER AMPLITUDE,
HIGHER FREQUENCY SIGNALS

FIG. 2F

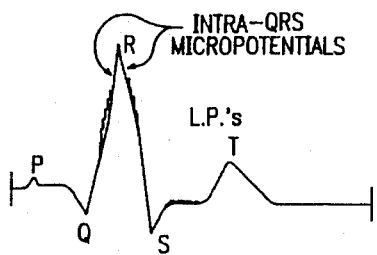

INTRA-QRS
MICROPOTENTIALS

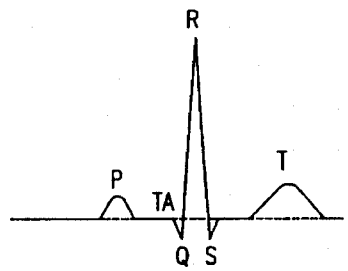

FIG. 2D

P WAVE – ATRIAL DEPOLARIZATION
TA WAVE – ATRIAL REPOLARIZATION MAY OCCUR
PR INTERVAL – ATRIO-VENTRICULAR
             CONDUCTION TIME 0.12-0.22s
QRS SEGMENT – VENTRICULAR DEPOLARIZATION            0.1s MAX
T WAVE – VENTRICULAR REPOLARIZATION
ST SEGMENT – ISO ELECTRIC
QT INTERVAL–

APPARATUS AND METHOD FOR PREDICTING CARDIAC ARRHYTHMIA BY DETECTION OF MICROPOTENTIALS AND ANALYSIS OF ALL ECG SEGMENTS AND INTERVALS

BACKGROUND OF THE INVENTION

The invention relates to electrocardiography (ECG), and more particularly to an improved electrocardiographic apparatus and method for predicting potential ventricular tachycardia and other forms of cardiac arrhythmia by the analysis of all ECG segments and intervals through the use of computer-supported analysis of selected signal components in ECGs, wherein, after preamplification and impedance transformation, signals are incrementally amplified, normalized, analog to digital converted, stored in memory, and manipulated by computer to provide frequency information about selected components of the signals.

After a myocardial infarction (M.I.) patients are at risk from the occurrence of dangerous disturbances of the cardiac rhythm, ventricular tachycardia. Sudden death from acute cardiac arrhythmia, in particular ventricular tachycardia, is a major risk in the first few hours after a myocardial infarction. During the first days after a myocardial infarction the incidence of ventricular arrhythmia is approximately 90%. The incidence of arrhythmias decreases considerably after the first several days but is still a substantial risk to the myocardial infarct patient. Five to ten percent of the post-infarct patients die within one year from sudden rhythmogenically caused cardiac death. Statistically, without treatment, approximately 50% of all myocardial infarct patients will eventually die of ventricular tachycardia.

Previous methods for identifying this risk group, e.g., long-time or Holter ECG, exercise test, resting ECG either are not sensitive enough or not specific enough. In the 1970s, minute signal fluctuations (of about 1 to 5 μV amplitude) were discovered in the surface ECG during sinus rhythm at the end of the QRS complex. These so-called late potentials occur significantly more frequently in post-infarct patients at risk of disturbance of rhythm than in patients with a good prognosis.

U.S. Pat. Nos. 4,422,459 to Simson teaches that a series of successive ECG waveforms may be captured, converted into digital form, and averaged together (after the exclusion of abnormal or non-typical waveforms) to provide a relatively noise-free composite waveform. Simson filters this averaged waveform using reverse or bi-directional filtering with a high-pass filter having a corner frequency of 25 Hz. Simson then computes the root-mean-square (RMS) value of the voltage in the filtered tail segment of QRS complex. In addition, Simson measures the width of the QRS complex after the filtering. Simson uses the RMS voltage measurement and the QRS width measurement as indications of whether or not the patient is likely to be subject to ventricular tachycardia.

The Simson method may be inapplicable to patients suffering from bundle branch block. It cannot always distinguish between meaningful high frequency components at the trailing edge of the QRS complex, which may indicate a predisposition to ventricular tachycardia, and noise that originates from power line disturbances or skeletal or smooth muscles or the like.

To extract more useful diagnostic information from the ECG signal, researchers have utilized Fourier transformations to process ECG waveforms. See, e.g., Cain, M. E., et al., "Quantification of Differences in Frequency Content of Signal-Averaged Electrocardiograms in Patients With Compared to Those Without Sustained Ventricular Tachycardia." Vol. 55, American Journal of Cardiology, 1500 (Jun. 1, 1985), showing frequency domain representations of the ECG X, Y and Z lead signals from patients with and without ventricular tachycardia. Energy, expressed as voltage squared, is plotted against frequency. The Cain et al. analysis was limited to a single Fourier transformation of a lengthy segment that included both the 40 millisecond terminal portion of the QRS complex and also the entire ST part of an averaged ECG waveform preprocessed with a Blackman-Harris window function to minimize spectral leakage. Cain, et al.'s analysis of the frequency domain data was limited to the frequency range of from 20 Hz to 50 Hz. Cain, et al.'s rationale for performing Fourier analysis of such an extended length segment, treating it as a single unit, was to "enhance frequency resolution."

Frequency domain techniques for locating small potentials often contain obscured voltages due to the relative size of the QRS complex in the ECG waveform. With Fourier transform techniques even small segments containing little information must also be windowed, further reducing information content and yielding a frequency domain representation that has too low a resolution to be useful in the determination of the presence or absence of micropotentials of a selected frequency range. Adapted autoregressive mathematical models for calculating the frequency power spectrum have been used for ECG signal frequency analysis. These mathematical methods enable an analysis to be performed by means of the so-called "maximum entropy method" (MEM), or by means of the so-called "adaptive filter determination" (AFD) which is related to the so-called "fast adaptive forward/backward least-squares method." See, Haberl et al. U.S. Pat. No. 5,211,179. Such methods were developed for calculating the optimum order of the autoregressive model and eliminating interfering low-frequency fundamental oscillations. The aforementioned signal processing methods are particularly well adapted for the analysis of ECGs.

U.S. Pat. No. 5,109,862 to Kelen et al. discloses a system which can receive X, Y and Z lead electrocardiographic signals, digitize the signals and signal average them. The second derivative or "acceleration" of the signals is then derived and a Blackman-Harris window is applied to the resulting vector, which is then operated upon by a fast Fourier transform (FFT) to yield a spectrum. Kelen et al. process the terminal portion of the QRS signal to attempt to find late potentials and rely upon samples of overlapped time segments. A "spectral entropy" calculation is performed, which in some sense is related to the topography of pseudo three-dimensional spectral plots. The teachings of Kelen et al., however, are not directed to measuring the intra-QRS signals per se.

U.S. Pat. No. 5,092,341 to Kelen discloses a system related to the system disclosed of Kelen et al., supra. The Kelen system is directed to addressing the limitation of prior late potential analysis systems, particularly time domain systems such as that of Simson. Kelen discloses that arrhythmogenic abnormalities are indicated by frequent and abrupt changes in the frequency spectrum of the QRS wavefront velocity as it propagates throughout the ventricle around regions of abnormal conduction thereby resulting in a high degree of spectral turbulence. A high degree of spectral turbulence of the overall QRS signal during sinus rhythm is considered indicative of an anatomic-electrophysiologic substrate for reentrant tachyrhythmia regardless of the detection of late potentials in the terminal QRS region of the digitized averaged electrocardiographic signal. Observations, measurements and calculations are made generally upon the QRS complex as a whole and not upon any portion arbitrarily identified by a temporal frequency or amplitude characteristic.

U.S. Pat. No. 5,271,411 to Ripley et al. discloses a system for detecting premature ventricular contractions and quantifying cardiac arrhythmias. Ripley et al. include a plurality of channel connectors connected to a multiplexer that feeds a filter bank with analog electrocardiographic signals. Generally, by extracting morphology information from an electrocardiographic signal in order to group heartbeats into similar classes information for morphologically similar beats can be used to assist in determining whether a given beat is normal or an abnormal beat, such as a premature ventricular contraction.

U.S. Pat. No. 5,199,438 to Pearlman discloses a microcomputer-based system for determining cardiac power. Pearlman determines cardiac the pumping power in terms of the time rate of change of mechanical energy developed by the left ventricle of a human heart. The system includes an occlusive cuff blood pressure monitoring system, a gamma camera, an echocardiogram system, an electrocardiograph system, and a Doppler ultrasound blood flow sensor all providing signals to a microcomputer. Pearlman defines cardiac power as the time derivative of the product of cardiac volume and cardiac or aortic pressure. A cardiac power index is the slope of the portion of the power-versus-time curve from the onset of systole to the moment when maximal power occurs. The cardiac power index is used to determine ventricular performance during the ejection portion of the cardiac cycle.

U.S. Pat. No. 4,680,708 to Ambos et al. discloses a frequency domain technique for late potential analysis using the Fourier transform on a signal segment in the terminal QRS region. Areas under the high and low frequency bands are calculated from the resulting spectral curve, and area ratios are determined.

Ambos et al. and Cain et al., have more recently attempted to study single-segment FFT results of selectively band-filtered signal averaged electrocardiographic (SAECG) signals from the entire cardiac cycle. They addressed the problem of extracting information on micropotentials within QRS complexes, typically obscured by the relatively very large and high slew-rate QRS morphology, by applying digital band-pass filters. Their frequency range of interests, however, have been confined to 70–128 Hz and much lower.

U.S. Pat. No. 5,215,099 to Haberl et al. teaches spectral temporal mapping (STM) of windowed Fourier transforms on overlapping segments of the terminal QRS, and early ST region for late potential analysis in the frequency domain. The result is a pseudo 3-dimensional time-frequency-power spectral density (PSD) display. It has been shown that STM increases the sensitivity and specificity of the SAECG when used in conjunction with standard time domain techniques i.e., the Simson method. However, STM may be weak in reproducibility due to high noise sensitivity and the dependence of the resulting STM on precise QRS end-point determination.

In spectral turbulence analysis (STA), Kelen calculated the velocity of the SAECG data and then used the short-time Fourier transform on multiple overlapping segments, including segments within the QRS complex. As in Haberl's STM technique, the result was also a 3-dimensional time-frequency-power spectral density (PSD) display. However, this technique is handicapped in that the short time lengths offer limited frequency resolution, especially after multiplication by window functions. Furthermore, the calculations necessary to quantify "spectral turbulence" are relatively complex, and the resulting indices are difficult to comprehend when the resulting 3-dimensional maps are referenced visually.

It has been found that slurs and notches within the QRS complex were strongly correlated with the presence of myocardial infarction and coronary artery disease. Flowers et al., strengthened this association further by correlating QRS notching and anatomic identification of infarct scar. See, e.g., Flowers et al. "The Anatomic Basis of High Frequency Components in the Electrocardiogram", Circulation, 1969; 39:531, and Flowers et al. "Localization of the Site of Myocardial Scarring in Man by High-Frequency Components", Circulation, 1969; 40:927. Historically, narrow band analog filters were used in an attempt to characterize the frequency bands of normal and notched QRS complexes.

Atrial fibrillation is thought to be due to reentrant pathways in the atria. A patient who has atrial flutter or fibrillation is at risk for cerebrovascular accident or stroke, which is often disabling and potentially fatal. For atrial fibrillation to take place, the atrial myocardial substrate also requires areas of slow conduction to initiate and maintain the reentrant circuit. The non-invasive risk assessment of atrial fibrillation has recently been studied using P wave-triggered or aligned SAECG. Only the time domain approach has been utilized, primarily because of the lack of commercially available signal processing packages for frequency domain analysis of the P wave. The main criterion has been reported by Guidera and Steinberg and Fukunami et al, as well as other independent researchers, to be the prolonged signal-averaged total filtered P wave duration. See, e.g., Guidera, S. A., Steinberg, J. S., "The Signal-Averaged P Wave Duration: A Rapid and Noninvasive Marker of Risk of Atrial Fibrillation," J Am Col Cardiol, 1993; 21:1645–51, and Fukunami M, et al. "Detection of Patients at Risk for Paroxysmal Atrial Fibrillation During Sinus Rhythm by P Wave-Triggered Signal-Averaged Electrocardiogram," Circulation, 1991; 83:162–169. No filtering standards have yet been established, hence the time domain criteria suggested by these authors are specific to their techniques used. A prolonged P wave duration in the time domain is thought to be a non-invasive indicator of the presence of delayed activation in the atria.

In patients with mitral stenosis or Wolff-Parkinson-White syndrome, it is difficult to determine the P wave endpoint for time domain analysis. Yamada and Fukunami et al., therefore had reported a spectral method for P wave analysis using area ratios, similar to the method that Cain and Ambos used for late potential analysis. See, Yamada T, et al. "Characteristics of Frequency Content of Atrial Signal-Averaged Electrocardiograms During Sinus Rhythm in Patients with Paroxysmal Atrial Fibrillation," J Am Col Cardiol, 1992; 19:559–63. They did not perform their analysis beyond 50 Hz. However, their technique has not been used in a widespread fashion, and had lesser sensitivity and specificity than time domain P wave analysis results.

Present methods of late potential analysis utilize both time and frequency domain methods. Existing frequency domain techniques require sensitive determination of the QRS end-point, or derivation of several statistical indices derived from complex mathematical algorithms involving multiple interslice correlation statistics of "spectral turbulence" information. However, all such techniques are not as well accepted as the conventional time domain Simson method, when comparing reproducibility, sensitivity and specificity of the results. The time domain method is not without limitations either. It cannot be used to analyze the SAECG signals in patients with conduction delay problems, and has a low positive predictive accuracy.

Delayed activation and abnormal recovery is well documented in the study of "late potentials." They are described as surface manifestations of alterations in conduction patterns through necrotic or fibrotic heart tissue in post-myocardial infarction patients at risk for sudden cardiac death. Fragmented conduction patterns should not manifest in SAECG signals acquired from patients without previous myocardial damage, because healthy heart tissue would form a more homogenous electrical conduction substrate compared with damaged tissue. In the latter case layers of damaged or necrotic tissue would break up or "diffract" the electrical conduction wavefront and form small amplitude, high frequency "interference patterns" along the conduction pathway. Having this type of tissue substrate predisposes the patient to experiencing life threatening re-entrant ventricular arrhythmias. It is believed that atrial flutter and fibrillation also stems from a substrate supportive of reentrant pathways. Such patients are associated with a high incidence of cerebrovascular thromboembolism, i.e. stroke.

In the past ten years, the SAECG has emerged as an increasingly valuable non-invasive tool for evaluating patients with known or suspected ventricular arrhythmias. Simson initially described the use of SAECG to determine the presence of late potentials as small amplitude, high frequency signals in the terminal QRS and early ST segment of the SAECG. They are thought to correspond with delayed cardiac activation, and are believed to indicate the presence of an underlying myocardial substrate for reentrant ventricular arrhythmias. Simson initially found late potentials in post-myocardial infarction patients with sustained ventricular tachycardia. It has also been shown that the presence of late potentials is indicative of inducible ventricular tachycardia during electrophysiology study, as well as other post-myocardial arrhythmic events. Signal averaging has also been used to study patients presenting with syncope of unknown origin. Furthermore, signal averaging has been used in conjunction with left ventricular ejection fraction (LVEF) tests to manage survivors of acute myocardial infarction. If the patient's LVEF>40%, and SAECG time domain results are negative, then further expensive electrophysiology testing is not recommended for the patient. The question is what happens if the SAECG test is positive, i.e. how accurate is the test in predicting patient risk for developing either spontaneous or inducible, sustained ventricular tachycardia? While the SAECG time domain results have a very high negative predictive value, they unfortunately also have a low positive predictive value.

SUMMARY OF THE INVENTION

It can be postulated that if damaged myocardial substrate exists, then micropotentials should be detected not only in the terminal QRS and early ST region i.e., late potentials, but also during the early phase of ventricular depolarization, i.e. throughout the QRS complex. High frequency micropotential detection and analysis of all ECG segments and intervals may also prove useful, but verification of very small potentials in a waveform reaches the boundary of what is technically possible. The fast up and down slopes of the QRS waveform morphology have prevented close examination of the entire QRS signal by conventional frequency domain methods. Techniques which are confined to the analysis of terminal QRS and the early ST segment do not detect diagnostically significant signals in other ECG intervals, such as those within the QRS complex itself. Hence, there exists a need for a robust yet straightforward frequency domain methodology which addresses the weaknesses in the present frequency domain methods, while permitting the analysis of not only the late potential region but other ECG segments corresponding to ventricular depolarization and repolarization. Once the challenge of being able to analyze the intra-QRS region is met, then the analysis of other ECG segments, such as the intra-P wave region may follow using the same underlying methods.

While the aforementioned prior art approaches to the problem both recognize that the presence of high frequency components in various portions of the ECG waveform can identify patients likely to experience cardiac arrhythmia, these approaches do not adequately address the practical problem of providing the physician with clear and unambiguous, reproducible information presented in a form that is simple to understand and utilize. Thus, it would be desirable to indicate cardiac arrhythmia by analysis of all ECG segments and intervals to detect micropotentials in order to screen and identify cardiac patients at risk of potentially lethal atrial and ventricular arrhythmias without excluding bundle branch block patients.

It is an aspect of the present invention to provide an apparatus and method which not only can analyze the terminal QRS and early ST region for late potentials, but also the intra-QRS region of the R wave-triggered SAECG for the existence of high frequency micropotentials. These signals indicate the presence of electrical fragmentation in the myocardium and are indicative of a patient at risk for ventricular tachycardia or other arrhythmias.

A further objective is to permit the acquisition of P wave-triggered SAECG and the frequency domain analysis of the P wave to study patients at risk for atrial fibrillation and flutter, thus not being limited to the R wave region of the SAECG, but instead permitting spectral visualization and analysis of the intra-QRS region. Additionally, the apparatus and method are useful for the analysis of all other SAECG regions, including the HIS bundle (P-R interval) and T wave regions.

In addition to recognizing that frequencies at and above 50 Hz are useful and meaningful, analysis of such high frequency components uses a determination of the background levels of such components and a comparison of these background levels with the level of similar components in the trailing portions of the QRS complex and the ST part where their presence may be indicative of tachycardia. The presentation of the information to the physician is provided in a way that is readily understandable and usable without the need for extensive training.

An embodiment in accordance with the invention extracts a high frequency signal "signature" of damaged myocardium throughout the entire QRS complex. Instead of measuring areas under the spectral curve and calculating area ratios as by Cain, or calculating a normality factor as by Haberl, or interslice correlations as by Kelen, it quantifies the increase or decrease of the presence of spectral peaks in the 50–300 Hz range using a "Spectral Change Index". It does not require precise end-point or other fiducial point determination, nor pre-filtering of the raw signal, hence it provides a necessary tool for both intra-P wave and intra-QRS analysis. It uses a large analysis window size (e.g. 300 points for intra-QRS analysis) which optimizes the performance of the Fourier transform.

The novel frequency domain technique for the noninvasive detection and analysis of myocardial fragmentation uses a spectral transform of the second derivative (acceleration) of the signal-averaged temporal signal such as an FFT to examine large spans of digitized signal in specific ECG segments, thereby preserving the frequency resolution of the transformation. Hence, the technique does not limit analysis to the late potential region of the SAECG, but permits spectral visualization and analysis of the intra-QRS region, intra-P wave region, and other ECG intervals. An index of the degree of spectral fragmentation, known as the Spectral Change Index, is derived by taking the sum of the absolute Spectral Amplitudes (SA) at the k+1 frequency point subtracted from the SA at the k frequency points for integer k=50 to 299, e.g. 50 to 300 Hz, divided by the maximum SA in the bandwidth of interest, then multiplied by 100. The advantages of having a frequency domain technique for P wave analysis is that it can be used in conjunction with time domain measurements, particularly the filtered P wave duration, for improved risk stratification of patients prone to atrial fibrillation and flutter.

Briefly summarized, the present invention relates to an apparatus and method for the acquisition and analysis of electrocardiogram signals to non-invasively detect and quantify presence of abnormal cardiac conduction patterns in patients at risk of heart disease. A windowed Fourier transform of the second derivative (acceleration) of the signal-averaged ECG is calculated for particular regions of interest for each lead, including the intra-QRS, ST-segment, T and P wave regions. A quantitative index, the Spectral Change Index, is calculated from the resulting "acceleration spectrum" for each lead, as well as the composite (X+Y+Z) lead, to quantify the degree of spectral "fragmentation" to stratify patients at risk for potentially lethal cardiac pathologies.

A more detailed description of the preferred embodiment of the invention, and further objects and advantages of the invention, are set forth in the drawings, in the detailed description which follows, and in the claims annexed to and forming a part of this specification. The invention itself is defined with particularity in the claims.

BRIEF DESCRIPTION OF THE DRAWINGS

FIGS. 2A–2F illustrate attributes of an ECG waveform and particularly a single QRS complex by means of which the operation of the method and of the apparatus shown in FIG. 1 is explained;

DETAILED DESCRIPTION OF THE PREFERRED EMBODIMENT

Figure 1:
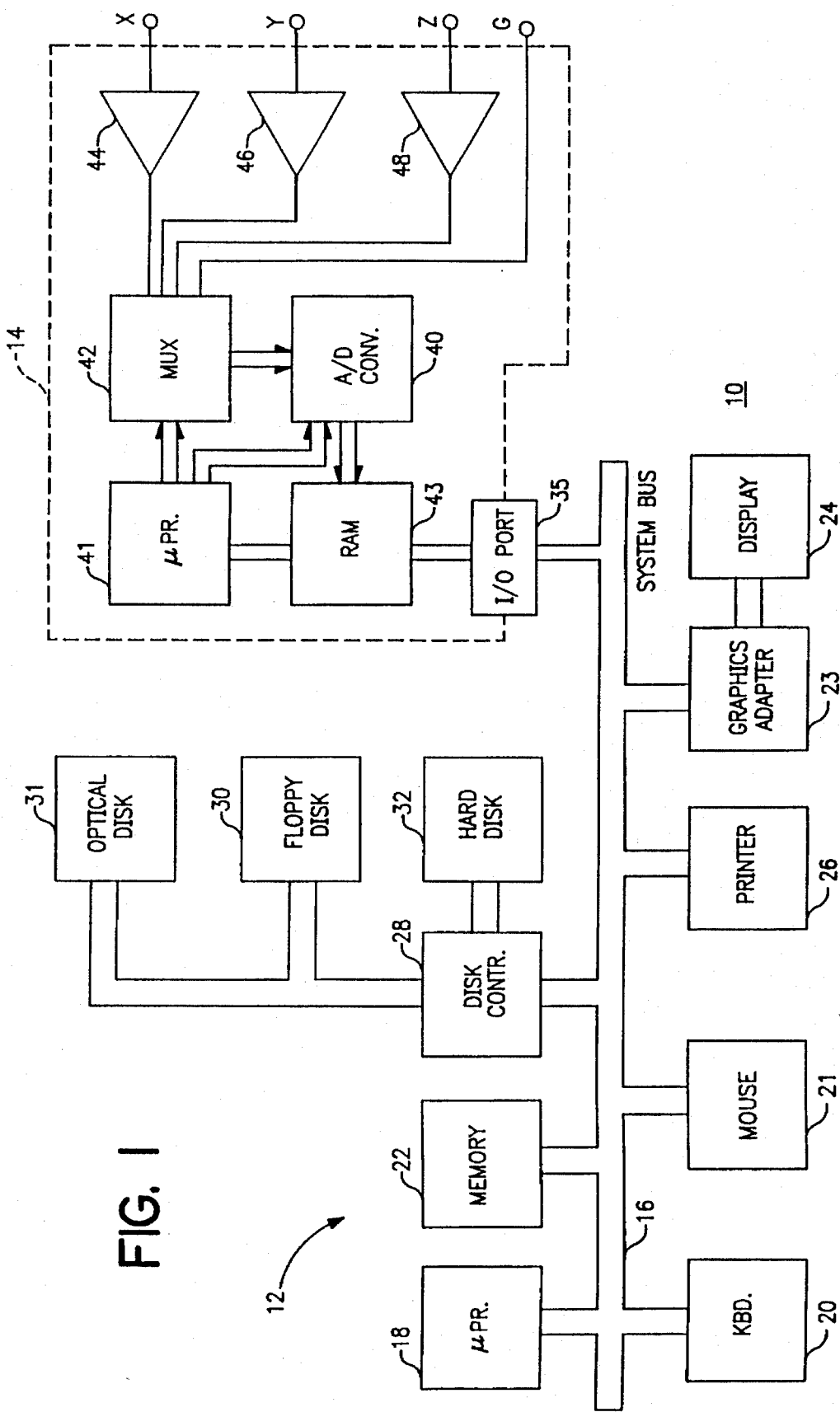
FIG. 1 is an overview block diagram of an apparatus embodying the present invention and having a signal acquisition unit for collecting ECG signals from a human body and a computer for processing such signals.

Referring to the drawings, and especially to FIG. 1, an apparatus embodying the present invention is generally shown therein and is identified by numeral 10. The apparatus 10 comprises a conventional IBM PC compatible digital computer 12 having an electrocardiographic signal acquisition unit 14 connected thereto. The computer 12 includes a system bus 16 for carrying data, address, control and timing signals between the various modules of the computer 12, all of which are well known to those skilled in the art. A microprocessor 18 is connected to the system bus 16 for communication therewith. A keyboard unit 20 and a mouse unit 21 are connected to the system bus 16 for communication therewith, as is a memory 22, comprising both read only memory (ROM) and random access memory (RAM), a video display card or graphics adapter 23 and a display 24, and a printer 26. A disk controller 28 is connected for communication with the system bus 16, and a floppy disk 30, an optical disk 31 and a hard disk 32 are connected to the disk controller 28 for communication therewith as storage devices. All of these aforementioned elements comprise the conventional microcomputer system 12.

Also connected to the system bus 16 through a detachable serial, parallel, PCMCIA data link I/O port 35 is a portable signal acquisition unit 14 which, for example may be a real time acquisition module, e.g. a model 1200EPX, or computer peripheral cards, e.g. models LP-Pac Q, Predictor I and Predictor IIc signal-averaging system, which may be obtained from Arrhythmia Research Technology, Inc., Austin, Tex. Alternatively, the signal acquisition unit 14 may include off-line mode analog or digital storage, e.g., playback of Holter recorder data. This signal acquisition unit 14 includes a microprocessor 41 having a storage device and a RAM memory 43, that is battery powered to retain contents of the storage device for extended periods. The unit 14 also contains an analog-to-digital converter 40 that is connected to a multiplexer 42, and both are controlled by the microprocessor 41. The multiplexer 42 is connected to an X-lead bipolar electrocardiographic amplifier 44, a Y-lead bipolar electrocardiographic amplifier 46, and a Z-lead bipolar electrocardiographic amplifier 48, which are adapted to be connected via respective bipolar leads X, Y and Z and a ground lead G to a patient for the sensing of electrocardiographic signals from the patient's body, as is well known to those skilled in ECG technology.

In practice, a nurse carries the unit 14 to the patients, records their ECGs, and then connects the unit 14 to the computer 12 by plugging the unit 14 into the computer's I/O port 35 and commanding the two microprocessors 18 and 41 to transfer the digitized ECG signals from the RAM 43 to the RAM portion of the memory 22 and ultimately to the hard disk 32 under the software control.

Each of the amplifiers 44, 46 and 48 is a low-noise electrocardiographic amplifier that amplifies and passes signals from close to D.C. to an upper limit that falls within the range of about 300 to 500 Hz (at or below one-half of the sampling rate). These amplifiers 44, 46 and 48 are also designed to electrically isolate the lines X, Y, Z from all sources of power and from each other.

The multiplexer 42 and the analog-to-digital converter 40 enable voltage levels at the output of all three amplifiers 44, 46 and 48 to be sampled 1,000 or 2,000 times each second to produce digital signal samples from the output of each of the three amplifiers 44, 46 and 48. The signal acquisition unit 14 as used in the described embodiment, e.g., the LP-Pac Q, above, provides 0.625 μV LSB; resolution: 16 bits; dynamic range: +/−20.28 mV for analog-to-digital conversion.

The digital samples thus collected represent successive ECG waveforms. These samples are initially stored in the RAM memory 43. In a manner similar to that which is fully described in U.S. Pat. No. 4,442,459 to Simson, the samples for successive ECG waveforms each may be matched to a QRS template, and those samples corresponding to waveforms which do not match the template or which are otherwise abnormal are not retained. The remaining multiple digital samples representing a succession of input ECG waveforms can then be broken up into a plurality of arrays of digitized signals each containing the samples for one input ECG waveform. The digitized signals within each of these arrays are placed into phase with the signals from the other arrays, and the amplitudes of signal values representing waveform amplitude at corresponding points in time (relative to the QRS waveform) within the arrays are then averaged over many waveforms (for example, over 200 waveforms) to reduce the noise from muscle potentials and power line interference and the like to a minimum. This averaging process is preferably carried out with a resolution of at least 12 data bits. The resulting single array of averaged signals is ultimately transferred out of the RAM 43 conveyed across the I/O port 35, and stored on the surface of the optical disk 31 or the hard disk 32.

The array of averaged signals may contain only the average of just the X lead waveforms, or of just the Y lead waveforms, or of just the Z lead waveforms, alternatively, it may contain the sum of all of these separately-monitored X, Y and Z waveforms. The array which represents the time average of a series of ECG waveforms that were taken from a single patient, is then analyzed in accordance with the teachings of the invention.

The array of averaged signals may contain, e.g., 800 12-bit samples, and the samples are spaced apart in time from each other by one millisecond. The embodiment in its preferred form begins by amplifying (using a low-noise amplifier), filtering (with a low-pass filter having a cut-off frequency in the range of 300 Hz to 500 Hz), digitizing (at the rate of 1000 12-bit digital samples per second), and averaging together a large number (100 or so) of ECG waveforms, discarding nontypical waveforms.

The method of data acquisition employed uses a bipolar orthogonal XYZ lead system which supplies signals for signal average electrocardiographic data acquisition. The conventional bipolar orthogonal X, Y, Z (Frank) lead system is used for SAECG data acquisition. However, other lead arrangements may also be advantageous, e.g., "Lewis leads" may be used for detecting elusive small amplitude P waves. The signals are digitized summed for signal averaging to provide a time varying signal average electrical dipole signal for the X, Y and Z directions. The rate of change of each of the electric vectors is equal to the first derivative with respect to time of each of the components. The "acceleration" of the signal averaged electric field vectors is a second derivative with respect to time of each of the components. If a 1 kHz sampling rate is employed, typically the intra-QRS region is defined by a lower bound of about 150 milliseconds before the QRS offset and an upper bound of about 150 milliseconds after the QRS offset, making a window width of about 300 milliseconds. The acceleration spectrum can be found by applying the Fourier transform to the second derivative with respect to time of each of the lead signals, or of the composite lead signals, within the time window of interest. The Fourier transform is applied over 512 samples or points, with zero padded points. A Blackman-Harris tapering window may be used to reduce spectral leakage. Once the acceleration spectrum is calculated, an algorithm which has been disclosed automatically examines the bandwidth of interest from 50 to 300 Hz (see equations 5, 6 and Spectral Change Index programming discussed below).

The following steps comprise signal acquisition:
a. X, Y and Z orthogonal lead preamplification and amplification of ECG without notch filtering.
b. Digitizing the signals with an analog-to-digital converter of either 12, 14 or 16 bit resolution. Again, it should be noted that the data could also be stored on a Holter tape, then played back into the amplifier and digitized, or it could have been stored as a digitized signal on a digital Holter device, or it could have been stored on a nonportable digital archival device such as a read-writable optical disk or hard drive.
c. Triggering on either the R wave or P wave depending on whether the end-user desires to perform ventricular or atrial arrhythmia analysis, respectively. If the P wave is studied for the presence or absence of atrial pathologies, the SAECG should be acquired using P wave-triggered, P wave templated methods. This is necessary to preserve the atrial micropotentials which may otherwise be eradicated by P-R jitter, if P wave analysis was performed on R wave aligned signal-averaged ECG's.
d. Forming beat template from the first few/several incoming beats.
e. Using a template matching (e.g. cross-correlation) technique to select and align subsequent incoming beats.
f. Performing ensemble averaging until stop criteria is met, i.e. either noise level is low enough, or a certain number of beats has been averaged.
g. If the acquired ensemble average was R wave-triggered, then the QRS onset and offset are found. If the ensemble average was P wave-triggered, then the P wave onset and offset are found. Such an algorithm was developed as a modification of algorithms used for QRS onset and offset finding.
h. The ensemble averaged patient data, onset and offset parameters and other patient information are then stored on a storage device in a personal computer.

Note that the hardware configuration shown in FIG. 1, in which the computer 12 is used in conjunction with the signal acquisition unit 14, is only one of many possible configurations that may be utilized, when implementing the present invention. For example, all of the above could have been carried out by the computer 12, rather than by the unit 14, and the unit 14 could have been a simple accessory to the computer 12. The signal array could have been transferred from the unit 14 to the computer 12 on a floppy diskette or sent over a parallel data transmission channel, an infrared optical link, or a radio or magnetic coupling link. The computer 12 could have been omitted entirely, if the signal acquisition unit 14 were sophisticated enough to carry out the remaining steps and had a suitable printer or display or both.

Turning now to FIGS. 2A–2F, cardiac muscle action is illustrated showing attributes of the ECG waveform, and particularly that of a single QRS complex wherein intra-QRS micropotentials resulting from the muscle action of damaged heart tissue is indicated by FIG. 2E. FIGS. 2A and 2B show atrial systole and ventricular systole caused by heart muscle contraction initiated by electrical stimulation such that blood may flow into and out of the heart respectively.

FIG. 2C illustrates the myocardium, or the middle muscular layer of the heart wall, as a schematic representation of an action potential moving down the wall of the heart showing some of the ion current indicated by the circles of ion current flow causing depolarization in the direction shown by the arrow in the wall of the heart. Thus, propagation of an action potential in the wall of the heart, as shown, provides contraction of the heart muscle through electrical stimulation. The action potential movement constitutes a current which flows in a circulating path through heart tissue causing a voltage drop with the polarity shown. The region ahead of a propagating action potential is positive with respect to the region behind it, resulting in a potential difference in the tissue. Thus, current flows while the action potential is propagating mainly during the QRS wave of the ECG or during the recovery period of the T wave. As is well understood, conventional ECG apparatus measures such potentials on the surface of the body. FIG. 2D illustrates and identifies the ECG segments and intervals of the waveform cycle during one cardiac cycle. For illustrative purposes, the P wave (atrial depolarization) and the QRS segment (ventricular depolarization) include the atrial systole and ventricular systole described in connection with FIGS. 2A and 2B above.

FIG. 2E also shows an ECG waveform for a single heartbeat. However, here the ECG waveform shows manifestations indicative of patients at risk from the occurrence of dangerous disturbances of the cardiac rhythm (ventricular tachycardia). Here, late potentials (L.P.s) which are understood as being so indicative are shown in the ST segment found after ventricular depolarization of the QRS segment. Of particular interest in connection with the described embodiment, intra-QRS micropotentials are also indicated in the QRS complex shown in FIG. 2E, also referred to as notches and slurs. The underlying QRS signal has a lower frequency but much higher magnitude/amplitude than the micropotential signals. As discussed further, these relative magnitudes often obscure or impede the ability to discern the relevant intra-QRS micropotentials.

Turning now to FIG. 2F a schematic block diagram illustrates electrical conduction through healthy tissue 80 and damaged tissue 82 representative of heart tissue. As modeled, note that electrical conduction through healthy heart tissue provides unattenuated signals therethrough; while electrical conduction through damaged tissue results in micropotentials, e.g., smaller amplitude higher frequency signals. As described, delayed activation and abnormal recovery results in surface manifestations of alterations in conduction patterns through necrotic or fibrotic tissue in post-myocardial infarction patients or patients at risk for sudden cardiac death. Such are manifested as fragmented conduction patterns in representative frequency spectra due to the breaking up or diffracting of electrical conduction through damaged heart tissue. Thus, the quantification of the degree of this spectral fragmentation can serve to stratify patients at risk for potentially lethal cardiac pathologies.

The signal processing apparatus and method of the described embodiment detects fragmentation of electrical conductive patterns in necrotic or fibrotic cardiac tissue due to various signal artifacts in both the depolarization phase, as well as the repolarization phase, of the cardiac cycle. It is desirable to extract small amplitude, high frequency intra-QRS signals that are often obscured by the relatively large QRS morphology, the steep ascending and descending slopes of QRS waveform which in the past prevented close examination of the intra-QRS signal by conventional frequency domain methods, thus the increase or decrease of the presence of spectral peaks in the 50 to 300 Hz range is quantified using the Spectral Change Index. The method does not require precise endpoint or fiducial point determination nor does it require pre-filtering of the raw signal. The methodology operates under the principle of detecting diffracted or broken up electrical conduction wavefronts manifesting themselves in the form of small amplitude, high frequency "interference patterns" along the conduction pathway. The micropotentials result from diffraction or delays occurring in damaged or necrotic cardiac tissue.

Spectral analysis of the intra-QRS analysis region or intra-P wave region is typically defined in the system default mode by a 300 millisecond time segment starting at 150 milliseconds before the QRS offset and ending 150 milliseconds after the QRS offset. The end-user can redefine the location and duration of the analysis window by simple keyboard interaction with the apparatus.

In the same way, there are default values for P wave and ST-segment analysis, but the end-user always has the liberty to vary these settings. Since the technique hinges on well established mathematical principles, discussed below, it can be used as a "universal tool" for the frequency analysis of all ECG segments, including the P wave and T wave regions. The apparatus permits the user to move "start" and "end" electronic cursors to demarcate the segment to be analyzed. Naturally, the Spectral Change Index is thus characterized for different regions of analysis, to separate normal from abnormal data.

At any moment in time, the signal-averaged electrical vector E(t) of the heart recorded on the body surface can be expressed as the resultant of three signal-averaged directional electrical dipoles:

$$E(t)=E_x(t)+E_y(t)+E_z(t) \tag{1}$$

This is electrically equivalent to that which has been termed the "composite lead" in conventional SAECG analysis. The rate of change (velocity) of this signal-averaged electric vector is then:

$$E'(t) = \frac{dE(t)}{dt} = \frac{dE_x(t)}{dt} + \frac{dE_y(t)}{dt} + \frac{dE_z(t)}{dt} \tag{2}$$

Consequently, the acceleration of this signal-averaged electric vector is given by:

$$E''(t) = \frac{d^2E(t)}{dt^2} = \frac{d^2E_x(t)}{dt^2} + \frac{d^2E_y(t)}{dt^2} + \frac{d^2E_z(t)}{dt^2} \tag{3}$$

In present SAECG systems, either a sampling rate of 1 or 2 kHz is used. In an 800 millisecond and 1 kHz sampling rate record of the signal-averaged ECG file format of the embodiment, the intra-QRS region is typically defined by an upper bound of 600 milliseconds and a lower bound of 300 milliseconds, e.g., starting at 150 milliseconds before the QRS offset and ending 150 milliseconds after the QRS offset, as discussed above. The frequency spectrum of this acceleration vector, or "acceleration spectrum", can then be found by calculating the Fourier transform of the composite lead bounded by the time window of interest. In theory, the discrete Fourier transform operation can then be expressed as $$S_A(\omega) = \int_0^T E''(t)e^{-j\omega t}dt \tag{4}$$

In actual practice, the acceleration spectrum is calculated and analysis is performed for each orthogonal lead as well as the composite lead. For increased directional sensitivity, the amplitude and frequency of these high frequency micropotentials recorded in any of the X, Y or Z leads would be dependent on the extent of tissue damage in a particular direction.

For each lead, the following steps take place prior to Fourier transformation:

1. The DC bias of E"(t) is adjusted;

2. The resulting zero-mean data segment is then multiplied by a window function, such as a Blackman-Harris window. This windowing process serves to taper the truncated data segment, thereby minimizing "leakage" when taking the Fourier transform; and
3. The resulting zero-mean, windowed data is then normalized.

Hence, after DC bias adjustment, multiplication by a tapering window function, and normalization, the acceleration spectrum of the X-lead is calculated thus:

$$S_{x,A}(\omega) = \int_0^T E''(t)e^{-j\omega x}dt \quad (5)$$

where T=512. Note that the remaining points in the Fourier transformed array are null padded. Hence, if the end-user has selected 300 points for analysis, the last 212 points are set to 0. Acceleration spectra for the Y- and Z-leads are similarly calculated.

Once the acceleration spectrum is calculated, the algorithm automatically examines the bandwidth of interest, which is preset to 50–300 Hz. An index of the degree of spectral "fragmentation", the Spectral Change index, is formulated thus using discrete mathematics:

$$\text{Spectral Change Index} = \frac{\sum_{k=50}^{299} |(S_A(k+1) - S_A(k)|}{S_{A,max}} \times 100 \quad (6)$$

The numerator is a calculation of the sum of absolute spectral gradients, and the denominator $S_{A,max}$ is the maximum amplitude of all spectral peaks in the bandwidth of interest.

The Spectral Change Index determination is embodied as part of the software listing set forth below as appendix A. The manner in which the Spectral Change Index is performed is set forth in further detail in the code written in the Basic programming language as follows.

```
CHANCALC:

CHANO = 0
FOR QQ = 25 TO 150            'From 50 to 300 Hz
YY1 = FFTOUT(QQ,FFTN)
YY2 = FFTOUT(QQ + 1,FFTN)
grad = ABS(YY2 – YY1)
CHANO = grad + CHANO
NEXT QQ
CHANO = 100*CHANO/MAXVEC
```

The Spectral Change Index is therefore a measure of change in the spectral components within the specified bandwidth, unbiased by spectral voltage. For example, a relatively "flat" acceleration spectrum within the specified bandwidth would result in a small-valued index, whereas an acceleration spectrum with many different high frequency spectral components would result in a large-valued index.

In addition to the Spectral Change Index, the number of spectral peaks within the bandwidth of interest can also be counted (manually or automatically). This adds yet another quantitative value, which is potentially of diagnostic significance for this test.

Figure 3A:
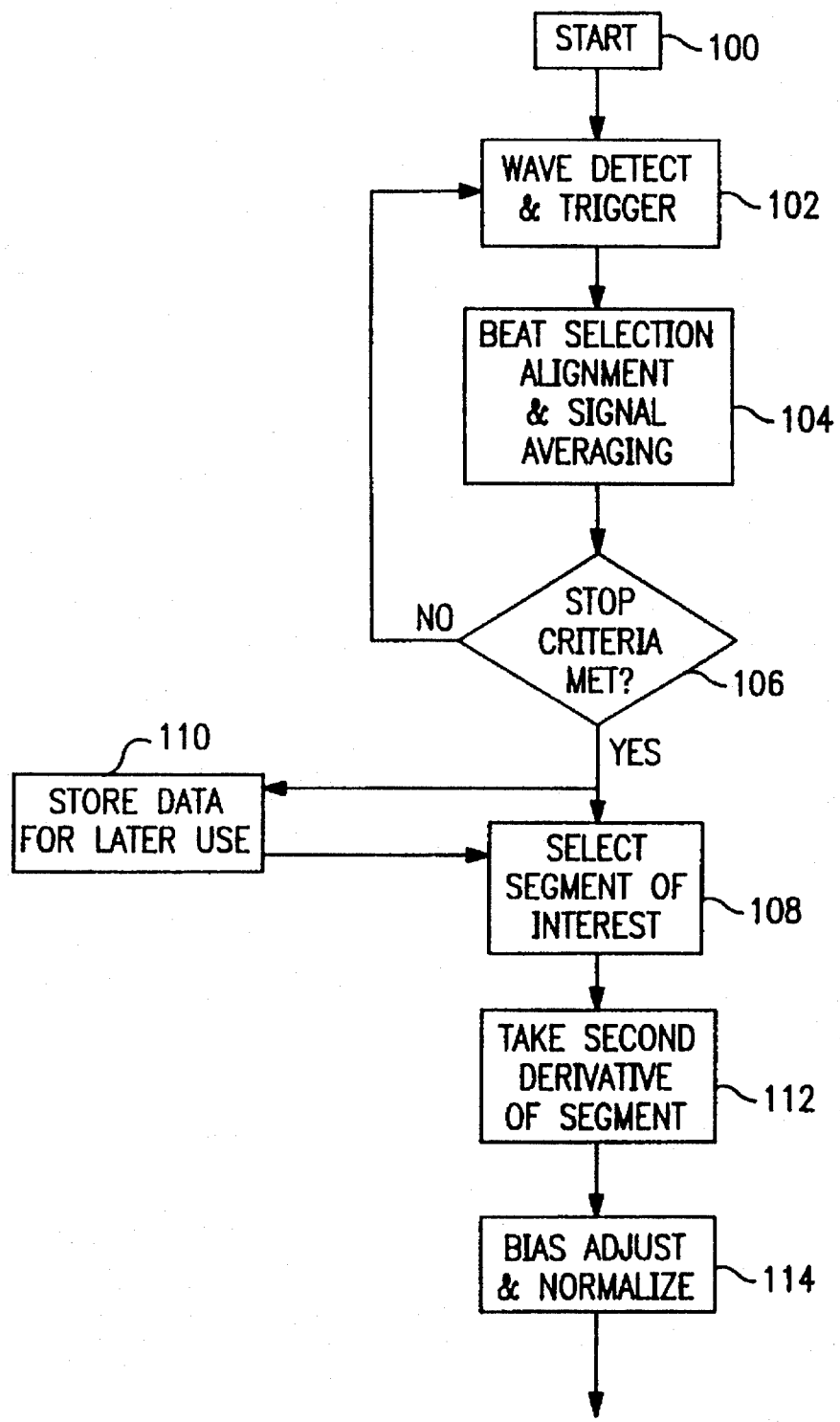
FIGS. 3A and 3B are a flow chart of some of the operations that are performed by the computer shown in FIG. 1.
Figure 3B:
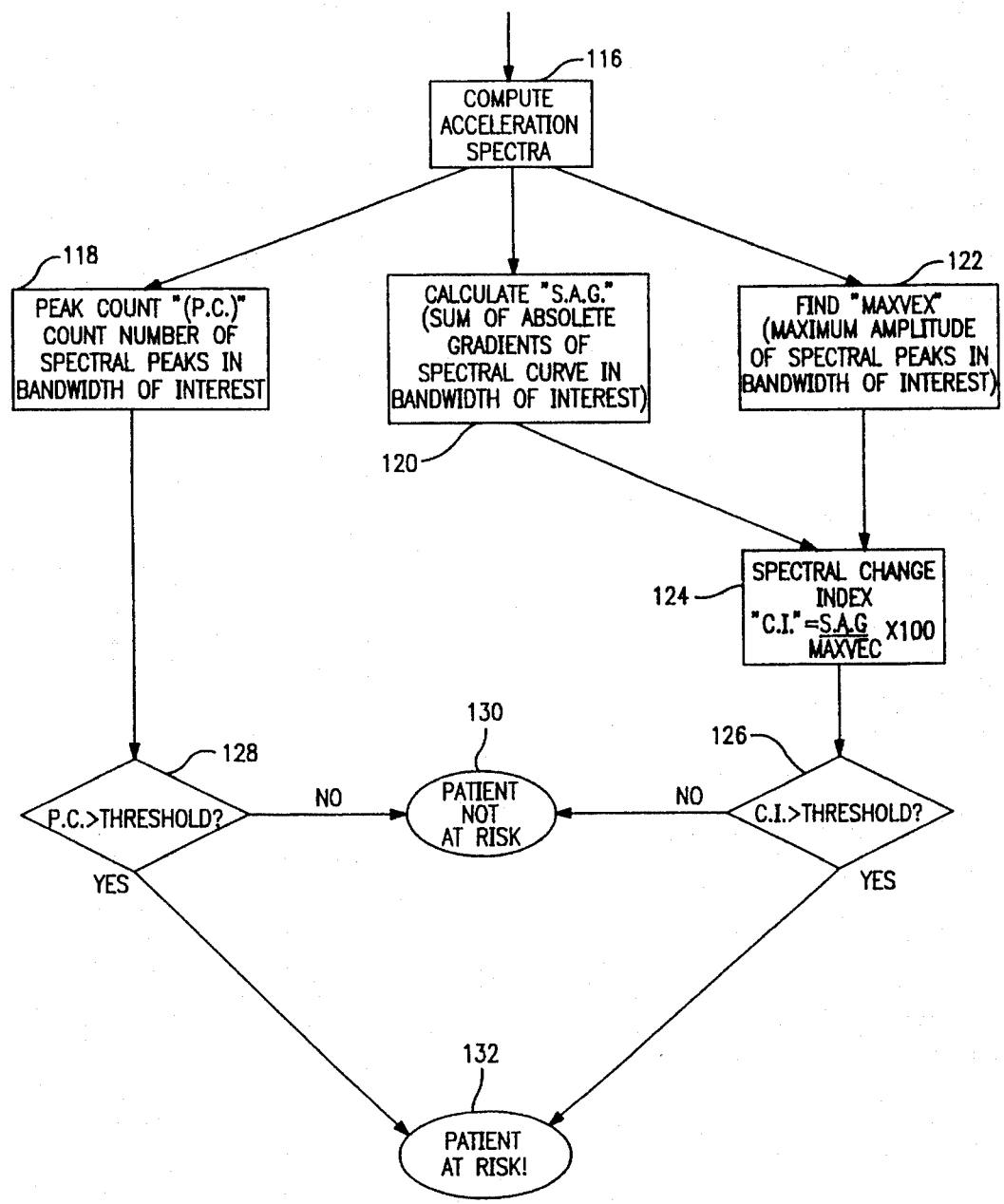

Turning now to FIGS. 3A and 3B, a program flow chart illustrates some of the operations that are performed in obtaining; (1) the Spectral Change Index, and (2) the peak count of the number of spectral peaks in the bandwidth of interest. Execution of the illustrated flow chart provides indications which may be interpreted by a doctor to determine of whether the patient is at risk through micropotential detection by quantifying the degree of spectral fragmentation within the bandwidth of interest. As may best be seen in FIG. 3A, the microprocessor 18 starts at starting step 100, and ultimately, from information provided at steps 130 or 132 as shown in FIG. 3B, a doctor may then make a determination of the patient either not being at risk or being at risk.

At step 102, the wave detect and trigger block is used for R wave or P wave detection and triggering. The detection and triggering is provided through the use of a template beat formation to detect and trigger upon an R wave or alternatively P wave of an ECG waveform. Thus, with micropotential detection according to the embodiment, a region of interest is selected of an electrocardiographic signal of one heartbeat. Also, to this end, at step 104 the selection, alignment and signal averaging is performed as described to average out noise to enhance the signal-to-noise ratio for the acquired data. A stop criteria determination for the signal averaging is determined at step 106 either through a determination that noise level is low enough or that a certain number of beats have been averaged. If the stop criteria of step 106 is not met, program flow returns to the wave detect and trigger block of step 102. If the stop criteria of step 106 is met, the program flow proceeds to step 108, select segment of interest. If R-triggered, the onset and QRS offset are determined in defining the segment of interest. If P-triggered, the P wave onset and offset are found in obtaining the segment of interest. At this point, the ECG data may be stored at step 110 for later use.

Proceeding to step 112, the second derivative of the segment is taken to generate a profile waveform representative of a temporal attribute of the segment of interest. The need for a temporal attribute, herein the second derivative, stems from the underlying QRS signal having a lower frequency but higher magnitude than the micropotential signals, therefore requiring a technique which will de-emphasize the low frequency components while enhancing the higher frequency components within the QRS complex. Since time domain methodologies, e.g., measurement of durations, RMS values, etc., cannot "focus on" or "tease apart" the micropotential signals from the fast upward and downward slopes of the QRS, a frequency domain approach is preferable. Nonetheless, the QRS complex itself represents a rapid slew rate of frequency change creating difficulties in the frequency domain as well, and thus the generation of a profile waveform representative of a temporal attribute of the region of interest will facilitate frequency domain analysis.

Invoking some established theorems for waveforms and their spectra, the Fourier transform relationship of the second derivative effectively increases the magnitude of the spectrum as a function of frequency. Hence, the amplitude of the spectrum increases as a function of frequency. Note particularly that a constant multiplier and a frequency variable multiplier are provided as "amplifying terms" therefore increasing as frequency increases providing the derivation of a frequency domain spectral representation of the profile waveform such that the frequency domain representation is representative of the segment of interest with the high frequency micropotentials being amplified therein. Thus, spectral energy at higher frequencies are selectively emphasized or enhanced.

The "differentiation" (first derivative) theorem for frequency domain transformation is as follows:

$$V'(t) \Leftrightarrow i2\pi f \cdot S(f) \quad (7)$$

Where V'(t) is the time derivative of the signal voltage as a function of time, t, and S(f) is the corresponding frequency domain representation as a function of frequency, f; constants in equation (7) and the equations following include the imaginary number i and the constant pi. Thus equation (7) would represent the velocity as a temporal attribute of the segment of interest, as opposed to the "acceleration" for a temporal attribute. Further derivatives of course further multiply or enhance higher frequencies. It was found that the acceleration spectra, however, adequately emphasizes the high frequency micropotentials for detection thereof. Taking the Fourier transform of the second derivative results as follows:

$$V''(t) \Longleftrightarrow (i2\pi f) \cdot (i2\pi f \cdot S(f)) \quad (8)$$

$$V''(t) \Longleftrightarrow -4\pi^2 f^2 \cdot S(f) \quad (9)$$

Therefore the "acceleration spectrum" is enhanced at higher frequencies attenuating lower frequencies and suppressing zero-frequency or D.C. components. In this way, the lower frequency components of the QRS are suppressed and the micropotential higher frequency components are greatly enhanced.

After taking the second derivative of the segment at step 112 to generate a profile waveform for use in the embodiment, D.C. bias adjustment e.g., mean removal is provided at step 114, by a bias adjustment and normalized block, which as discussed is provided for obtaining normalized segment data.

At step 116, the acceleration spectra is determined using Fourier transform techniques or other frequency transforms, e.g., adaptive filter determination (AFD), maximum entropy method (MEM), autoregressive (AR) process, moving average (MA) or autoregressive moving average (ARMA) processes. If Fourier transform techniques are utilized, then an appropriate window function should be used to window the data set. Once the acceleration spectra is computed, a bandwidth of frequencies in the spectral representation is defined. In the preferred embodiment 50 Hz to 300 Hz is utilized, however, this bandwidth may be altered or made variable for entry by the user.

A peak count (PC) is performed at step 118 to count the number of spectral peaks in the bandwidth of interest, which may advantageously be utilized to characterize the degree of variation within said bandwidth of interest of frequencies in said spectral representation to detect the micropotentials in the segment of interest of the electrocardiographic signal to quantify the degree of spectral fragmentation within said bandwidth of interest. In identifying a plurality of spectral peaks from the spectral representation for the frequencies within the bandwidth of interest, a determination is made using decision criteria for a percentage of maximum and minimum deflection to determine peaks and troughs e.g., 65% to 70% deflection. Once the peaks are identified they are counted and the counting of the spectral peaks is used to detect micropotentials in the region of interest of the electrocardiographic signal to quantify the degree of spectral fragmentation within the bandwidth of interest.

Steps 120 and 122 facilitate the computation of the Spectral Change Index at step 124. At step 120 gradients of the spectral curve in the bandwidth of interest are determined from the spectral representation for each of a plurality of frequencies within the bandwidth of interest. In the embodiment, each frequency representation from 50 Hz to 300 Hz, as indicated above, is used to sum the absolute gradients of the spectral curve. In step 122 "MAXVEC" is determined by the program as the maximum amplitude at spectral peaks in the bandwidth of interest to obtain a representative maximum amplitude of the spectral representation for the frequencies within the bandwidth of interest. Then, the Spectral Change Index (CI) provides a comparison between the representative maximum amplitude and the gradients, or sum of absolute gradients (SAG), from the spectral representation for each of the plurality of the frequencies to detect the micropotentials in the region of interest of the electrocardiographic signal to quantify the degree of spectral fragmentation within the bandwidth of interest. As discussed, according to the Spectral Change Index, the sum of absolute gradients is divided by MAXVEC and multiplied by 100 to determine the Spectral Change Index. In the described embodiment, the Spectral Change Index threshold of 15 is used to discern normal attributes from abnormal attributes, a low Spectral Change Index indicating a normal patient status.

At step 126 the Spectral Change Index is compared to the threshold to ascertain whether or not the patient under study is at risk, step 130 indicating that the patient is not at risk and step 132 indicating the patient being at risk. Similarly, the peak count is compared to a threshold in step 128 to determine whether the patient is at risk or not at risk. The Spectral Change Index threshold may be fixed or varied at user control, or alternatively two thresholds may be utilized to discern between borderline/abnormal patients by providing an intermediate Spectral Change Index count e.g., 16 to 20 as being indicative of borderline cases, requiring further study.

EXAMPLES

Figure 4A:
FIGS. 4A and 4B show normal X-lead ECG time and frequency plots respectively, for a person having a healthy heart.
Figure 4B:
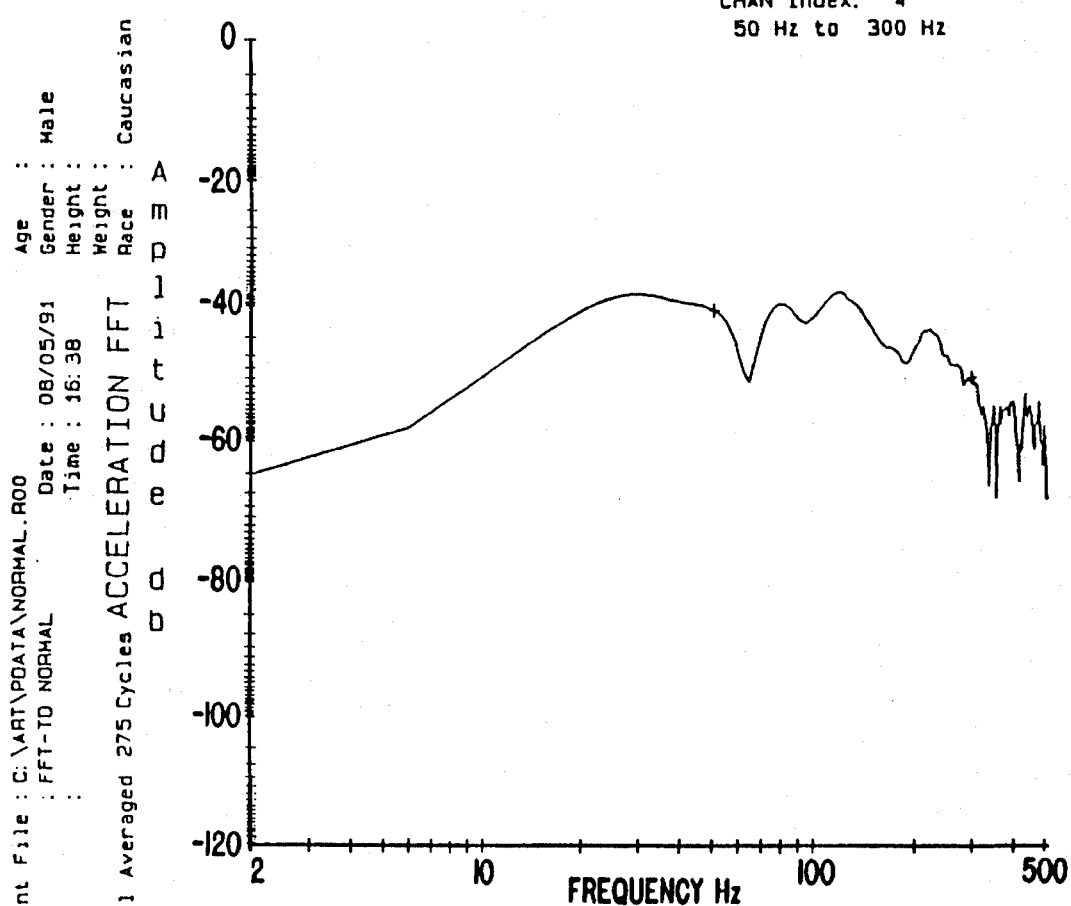
Figure 5A:
FIGS. 5A and 5B show abnormal X-lead ECG time and frequency plots respectively, of a post-myocardial infarction patient, a person at risk of potentially lethal cardiac arrhythmias.
Figure 5B:
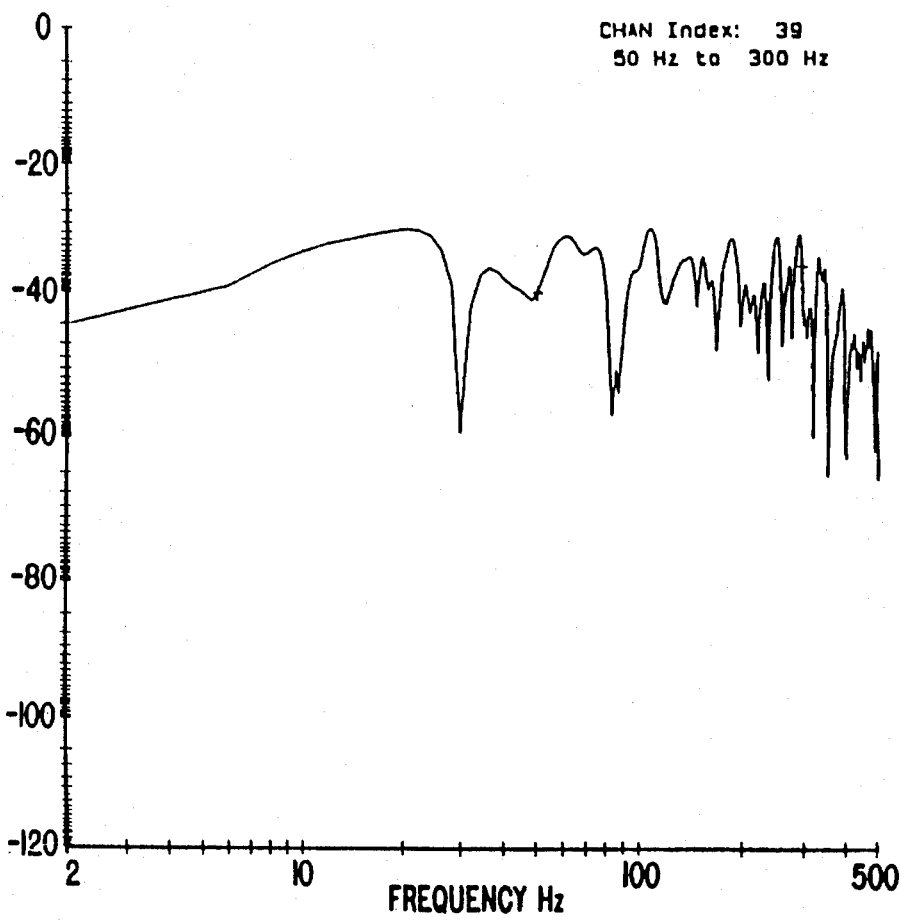

The apparatus was tested by employing previously collected data; for instance, from patients having evidence of involved myocardium such as a patient having sustained ventricular tachycardia. While the pilot study discussed herein shows the results for two individuals, further study would be appropriate. A subject with no cardiac disease typically displays a low Spectral Change Index, see e.g. FIGS. 4A and 4B (Spectral Change Index=4 for a normal patient), whereas patients presenting with myocardial damage, such as patients having late potentials detected by the time domain Simson method have a Spectral Change Index greater than 15, see e.g. FIGS. 5A and 5B (Spectral Change Index=39 for an abnormal patient).

Example results indicate that there are many individual spectral peaks within the 50 to 300 Hz bandwidth of the acceleration spectrum when the patient has evidence of involved myocardium, such as a patient with sustained VT. See FIG. 5B. One could postulate that the increase in these high frequency spectral components is caused by fragmentation of the wave of electrical activation in damaged, post-infarct myocardium. The example shows that subjects with no cardiac disease typically have a low Spectral Change Index (C.I.), whereas patients presenting with myocardial damage, such as patients with late potentials found by the time domain Simson method, have a C.I.>15. The study analyzed 26 post-MI patients (6 with bundle branch block) with spontaneously occurring sustained ventricular tachycardia (VT) and 20 control subjects without VT. In the spontaneous VT group, 19 of 26 patients had electrophysiology study (EPS) and all were inducible to sustained VT. Reproducibility (R) of C.I. was defined as the subject staying "normal" (or "abnormal") each time data from the subject was acquired and analyzed. R was studied for 8 subjects from the entire cohort. Results for C.I. in identifying patients at risk for (1) spontaneous, sustained VT, and (2) inducible VT during EPS, are summarized in Table I.

TABLE I

Sensitivity, Specificity, Positive and Negative
Predictive Accuracy, and Reproducibility for Spectral
Change Index in an initial cohort of 26 post-MI patients
and 20 control subjects.

| C.I. | Sens. | Spec. | +PA | −PA | R |
|---|---|---|---|---|---|
| Spont. VT | 77% | 85% | 87% | 74% | 100% |
| Induc. VT | 75% | 85% | 83% | 77% | 100% |

These results indicate that the embodiment of the apparatus and method has the potential to be a robust technique based on principles of cardiac electrophysiology as well as straight-forward but well established mathematical and signal processing techniques. The methodology yields results which are consistent with time domain results, and provides excellent reproducibility.

The study on post-MI patients shows that this new method has high specificity and positive predictive accuracy, and excellent reproducibility for the risk stratification of VT-prone post-MI patients, even for those with bundle branch block. Since the negative predictive value of the time domain SAECG test is very high, but has poor positive predictive accuracy (Simson method), the use of this new technique serves to fill a need in the field of signal-averaged ECG.

While a preferred embodiment of the invention has been shown and described for the apparatus and method for predicting cardiac arrhythmia by detection of micropotentials and analysis of all ECG segments and intervals, other embodiments of the present invention will be readily apparent to those skilled in the art from consideration of the specification and practice of the invention disclosed herein. It is intended that the specification and examples be considered as exemplary only, with a true scope and spirit of the invention being indicated by the following claims.

APPENDIX A

```
' ACCEL.BAS MAIN MODULE
' Version 1.0,
' This main module calls companion module ACCELCOM.BAS ' Copyright Arrhythmia Research Technology, Inc., 1995.  All rights reserved.

'"Store Analysis Settings
'"DIF Output
'------------------------------- LOCAL SUBROUTINES
        DECLARE SUB FFTDISP ()
        DECLARE SUB FFTMATH ()
        DECLARE SUB FFTOPT ()
        DECLARE SUB FFTPEAK ()
        DECLARE SUB FFTPLOT ()
        DECLARE SUB FFTPREP ()
        DECLARE SUB FFTSEG ()
'------------------------------- COMMON MODULE SUBROUTINES
        DECLARE SUB CHKCRT ()
        DECLARE SUB CLEARBOT (BLN, NLN)
        DECLARE SUB CLINE ()
        DECLARE SUB CPRT ()
        DECLARE SUB GETFDATA ()
        DECLARE SUB INITPLOT ()
        DECLARE SUB PLOTDATA (POUT$)
        DECLARE SUB PLOTDEMO ()
        DECLARE SUB RAWDRAW ()
        DECLARE SUB SELWIND ()
        DECLARE SUB SHOWDATA ()
'------------------------------- COMMON MODULE
        DECLARE FUNCTION XKEY ()
'------------------------------- LOCAL VARIABLES
        COMMON SHARED /FFTAR/ ACCEL(), FFTOUT(), SEGM(), WIND()
        COMMON SHARED /FFTAR1/ AR(), FIXF(), FIXM(), PEAKF(), PEAKM()
        COMMON SHARED /FFTNVAR/ FFTN, MAXVEC, SCY, SCYY, DB
        COMMON SHARED /FFTSTR/ WIN$, LL$, PWR$
        COMMON SHARED /FFTVAR/ WIN, LL, PWR, DCYN
        COMMON SHARED /FFTANS/ CI, AR, ARN, AMAXV
        COMMON SHARED /FFTAUTO/ AUTOPROG, AUTOXYZ, DISP3
'------------------------------- COMMON VARIABLES
        COMMON SHARED /PROGID/ PROG$  'ER$
        COMMON SHARED /ARRAYS/ INN$(), X,Z()
        COMMON SHARED /FILENAMES/ IFILE$, PFN$
        COMMON SHARED /DEMO/ ECGLEN, SID1$, STD1$, STU1$, STS1$, SSW1$
        COMMON SHARED /DEMO1/ ECGCK, STU$, STS$, SEQ, SNA$, SID$, SDA$, STI$
        COMMON SHARED /DEMO2/ SAG$, SEX$, SHT$, SWT$, SRA$, SM1$, SM2$, SSBP$
        COMMON SHARED /DEMO3/ SDBP$, SOP$, SC$, QRSON, QRSOFF
        COMMON SHARED /CONSTANTS/ ESC$, CRLF$, API, AE, ADB
        COMMON SHARED /SELWIND/ BW, EW, DELTA, FRWF
'------------------------------- ASSIGN SPACE (CALIFORNIA STYLE)
        DIM SHARED INN$(9)         '-------- COMMAND LINE STRINGS
        DIM SHARED XYZ(2400)       '-------- XYZ RAW ARRAY
        DIM SHARED LEAD(800)       '-------- RAW SEGMENT
        DIM SHARED DIFF(800)       '-------- 1st. DERIVATIVE OF RAW SAECG
        DIM SHARED ACCEL(800)      '-------- 2nd. DERIVATICE OF RAW SAECG
        DIM SHARED SEGM(512)       '-------- FFT WINDOWED SEGMENT
        DIM SHARED WIND(512)       '-------- FFT WINDOWED SEGMENT
        DIM SHARED FFTOUT(256, 40) '-------- MULTIPLE FFT ARRAY
        DIM SHARED PEAKF(15, 40)   '-------- FFT FREQ PEAKS
        DIM SHARED PEAKM(15, 40)   '-------- FFT MAG PEAKS
```

```
DIM SHARED FIXF(6, 40)    '--------- FFT FIXED FREQ
DIM SHARED FIXM(6, 40)    '--------- FFT FIXED MAG
DIM SHARED AR(7)          '--------- ANALYSIS RANGE 1=DL, 2=DH, 3=NL, 4=NH
'
ADB = 2.995732274#  '--------- CONSTANT LOG(20) TO LOG(10)
AE = 2.302585093#   '--------- SOMETHING
API = 3.141592654#  '--------- PI DEFINED
CRLF$ = CHR$(13) + CHR$(10) '--- CR LF CHAR
ESC$ = CHR$(27)    '--------- ESC CHAR
'------------------------------------ IDENTIFY PROGRAM
PROG$ = "IntraSpect"
VER$ = "1.00"
'------------------------------------ START IT A WHIRRIN'
DEF SEG = 0
ON ERROR GOTO 0
'------------------------------------ DECIPHER COMMAND LINE
CLINE
'------------------------------------ WHAT TYPE OF DISPLAY???
CHKCRT
'------------------------------------ PRINT PROGRAM NAME & VER
CPRT
'------------------------------------ RUN STRAIGHT THRU
'------------------------------------ GET A PATIENTS DATA
GETFDATA
'------------------------------------ SET VARIABLES TO DEFAULTS
AUTOPROG = 0: AUTOXYZ = 0: FFTN = 1
BW = QRSOFF - 150: EW = QRSOFF + 150
'BW = 300: EW = 600              ¥EC
WIN = 0: LL = 4: PWR = 1: DCYN = 1: DB = 1
AR(1) = 0: AR(2) = 25 '-----0-50Hz     ¥EC
AR(3) = 25: AR(4) = 150 '-----50-300Hz  ¥EC
ARN = 1
IF INN$(1) = "TUTOR.R99" THEN LL = 0 '---- COMPOSITE FOR TUTOR '------------------------------------ GET OPTIONS FOR FFT
FFTOPT
'------------------------------------ SELECT A SEGMENT
FFTSEG
'------------------------------------ SENSE AND SETUP MEAN X,Y,Z
IF LL = 4 THEN AUTOXYZ = 1: LL = 0 ELSE AUTOXYZ = 0

AFFT:  IF AUTOXYZ = 1 THEN
           DISP3 = 1
           LL = LL + 1
           FFTN = LL
           CALL CLEARBOT(18, 6)
       END IF
'------------------------------------ GET DATA READY
PFFT:  FFTPREP
'------------------------------------ RUN FOURIER TRANSFORM
FFTMATH
'------------------------------------ IF MEAN, RUN NEXT LEAD
IF AUTOXYZ = 1 AND LL < 3 THEN GOTO AFFT
'------------------------------------ SENSE PEAKS
FFTPEAK
'------------------------------------ DISPLAY FFT
FFTDISP
```

A-2

```
MLOOP: '--------- MENU ---- MENU ---- MENU ---- MENU ---- MENU
        CALL CLEARBOT(18, 6)
        COLOR 14, 0: LOCATE 18, 7
        PRINT "MAKE A SELECTION:"
        COLOR 11, 0
        LOCATE 19, 7: PRINT "1   FFT OPTIONS"
        LOCATE 20, 7: PRINT "2   ECG SEGMENT"
        LOCATE 21, 7: PRINT "3   RE-DISPLAY SPECTRUM"
        LOCATE 22, 7: PRINT "4   PLOT AS DISPLAYED"
        COLOR 12, 0: LOCATE 23, 7
        PRINT "5   EXIT"

IF AUTOXYZ = 1 THEN
           LOCATE 18, 45: COLOR 14, 0
           PRINT "SELECT ANALYSED LEAD:"
           LOCATE 19, 45: COLOR 11, 0
           PRINT "6   X-LEAD"
           LOCATE 20, 45
           PRINT "7   Y-LEAD"
           LOCATE 21, 45
           PRINT "8   Z-LEAD"
           LOCATE 22, 45
           PRINT "9   X,Y,Z / AVERAGE INDEX"
        END IF

IF CI = -1 THEN
           LOCATE 6, 10
           COLOR 4, 0
           PRINT "SETTINGS HAVE CHANGED, UPDATE DISPLAY WITH SELECTION 3    "
        END IF

COLOR 15, 0
        LOCATE 18, 40

NLOOP: VIEW
        QQ = XKEY '---------------------- WAIT FOR A KEY

IF QQ = ASC("1") THEN '---------------- GET FFT OPTIONS
           CI = -1
           DISP3 = 0
           IF AUTOXYZ = 1 THEN LL = 4
           FFTOPT
           CLS
           GOTO MLOOP
        END IF

IF QQ = ASC("2") THEN '---------------- GET FFT SEGMENT
           CI = -1
           FFTSEG
           CLS
           GOTO MLOOP
        END IF

IF QQ = ASC("3") THEN '---------------- DISPLAY

IF CI = -1 THEN
              '--------------------------------- SENSE AND SETUP MEAN X,Y,Z
              CALL CLEARBOT(18, 6)
              IF LL = 4 THEN
                 AUTOXYZ = 1
                 DISP3 = 1
                 LL = 0
              ELSE
                 AUTOXYZ = 0
              END IF
```

A-3

```
AFFTD:     IF AUTOXYZ = 1 THEN
                LL = LL + 1
                FFTN = LL
                CALL CLEARBOT(18, 6)
            END IF
            '--------------------------------- GET DATA READY
            FFTPREP
            '--------------------------------- RUN TRANSFORM
            FFTMATH
            '--------------------------------- IF MEAN, RUN NEXT LEAD
            IF AUTOXYZ = 1 AND LL < 3 THEN GOTO AFFTD
                FFTPEAK
                FFTDISP
            ELSE
                FFTDISP
            END IF

GOTO MLOOP
        END IF
        '
        IF QQ = ASC("4") THEN '---------------- PLOT / PRINT
          IF CI = -1 THEN
                BEEP
                LOCATE 8, 20
                COLOR 12, 0
                PRINT "PLOT DISABLED UNTIL DISPLAY IS UPDATED"
                GOTO MLOOP
          ELSE
                INN$(3) = "3"
                FFTPLOT
          END IF
          GOTO MLOOP
        END IF
        '
        IF QQ = ASC("5") THEN '---------------- SHUT IT DOWN
          CLOSE #1, #2, #3
          END
          GOTO MLOOP
        END IF
        '
        IF QQ = ASC("6") THEN '---------------- X-LEAD
          FFTN = 1
          DISP3 = 0
          LL$ = "X-Lead"
          FOR QQ = 1 TO 799: LEAD(QQ) = XYZ(QQ * 3): NEXT QQ
          FFTDISP
          GOTO MLOOP
        END IF
        '
        IF QQ = ASC("7") THEN '---------------- Y-LEAD
          FFTN = 2
          DISP3 = 0
          LL$ = "Y-Lead"
          FOR QQ = 1 TO 799: LEAD(QQ) = XYZ(QQ * 3 + 1): NEXT QQ
          FFTDISP
          GOTO MLOOP
        END IF
        '
        IF QQ = ASC("8") THEN '---------------- Z-LEAD
          FFTN = 3
          DISP3 = 0
          LL$ = "Z-Lead"
          FOR QQ = 1 TO 799: LEAD(QQ) = XYZ(QQ * 3 + 2): NEXT QQ
          FFTDISP
          GOTO MLOOP
        END IF
        '
```

A-4

```
        IF QQ = ASC("9") THEN '-------------------- X,Y,Z / MEAN AR
           DISP3 = 1
           FFTDISP
           GOTO MLOOP
        END IF

GOTO NLOOP

SUB FFTDISP
        CLS 0
        '---------------------------------- FFT AMPLITUDE GRID
        VIEW (50, 0)-(550, 221), 8, 0
        LINE (0, 0)-(512, 0), 15
        LINE (0, 0)-(0, 220)
        FOR YYY = 17 TO 230 STEP 17
        LINE (0, YYY)-(512, YYY), 15
        NEXT YYY
        '---------------------------------- FFT FREQUENCY GRID
        LINE (50, 0)-(50, 220), 15
        FOR XXX = 100 TO 550 STEP 50
        LINE (XXX, 0)-(XXX, 220), 15
        NEXT XXX
        '---------------------------------- FFT GRID TEXT
        COLOR 15, 0
        PPW = 1000 / SCY

IF DB = 2 THEN GOTO DVOLT

LOCATE 1, 70: PRINT 0; "dB"
        LOCATE 3, 70: PRINT -20 * PPW; "dB"
        LOCATE 5, 70: PRINT -40 * PPW; "dB"
        LOCATE 8, 70: PRINT -60 * PPW; "dB"
        LOCATE 10, 70: PRINT -80 * PPW; "dB"
        LOCATE 13, 70: PRINT -100 * PPW; "dB"
        LOCATE 15, 70: PRINT -120 * PPW; "dB"
        GOTO DHZ

DVOLT:  LOCATE 1, 70: PRINT 10 ^ (3 * PPW); "uV"
        LOCATE 3, 70: PRINT 10 ^ (2 * PPW); "uV"
        LOCATE 5, 70: PRINT 10 ^ (1 * PPW); "uV"
        LOCATE 8, 70: PRINT 10 ^ (0 * PPW); "uV"
        LOCATE 10, 70: PRINT 10 ^ (-1 * PPW); "uV"
        LOCATE 13, 70: PRINT 10 ^ (-2 * PPW); "uV"
        LOCATE 15, 70: PRINT 10 ^ (-3 * PPW); "uV"

DHZ:    LOCATE 17, 7
        PRINT "0   50   100  150  200  250  300  350  400  450  500 Hertz"

'---------------------------------- FIXED INSTRUCTION TEXT
        LOCATE 20, 12: COLOR 11, 0
        PRINT "CHAN Index:"
        LOCATE 23, 51: COLOR 14, 0: PRINT "<ENTER>"
        LOCATE 23, 59: COLOR 15, 0: PRINT "To Continue"
        '---------------------------------- DEFAULT TEXT
        IF DISP3 = 1 THEN
           LL$ = "X,Y,Z Mean"
           LOCATE 19, 12: COLOR 11, 0
           PRINT LL$
           LOCATE 20, 12: COLOR 11, 0: PRINT "CHAN Index:"
           LOCATE 23, 51: COLOR 14, 0: PRINT "<ENTER>"
           LOCATE 23, 59: COLOR 15, 0: PRINT "To Continue"
           FFTN = 1
        END IF
```

```
            CC = 11
            FOR QQ = 0 TO 799
            IF BW = QQ THEN CC = 12
            IF EW = QQ THEN CC = 11
            LINE (QQ / 3.1 + 200, (-LEAD(QQ) / 500) + 40 + YYYY)-(QQ / 3.1 + 200, (-LEAD(QQ + 1) / 500) + 40 +
            YYYY), CC
            NEXT QQ
            '
            LOCATE 19, 12: COLOR 11, 0
            PRINT LL$

DISP3L: CHANO = 0
            '------------------------------------ FFT GRAPH WITH COLORS
            FOR QQ = 0 TO 255      'EC Next line modified to handle log(0)
            F1 = FFTOUT(QQ, FFTN): IF F1 = 0 THEN F1 = .0000001
            F2 = FFTOUT(QQ + 1, FFTN): IF F2 = 0 THEN F2 = .0000001
            SYY1 = FIX(LOG(SCYY * F1 / MAXVEC) / AE * (SCY / 30))
            SYY2 = FIX(LOG(SCYY * F2 / MAXVEC) / AE * (SCY / 30))
            CC = 14
            IF QQ >= AR(1) AND QQ < AR(2) THEN CC = 9
            IF QQ >= AR(3) AND QQ < AR(4) THEN CC = 12
            IF QQ >= AR(1) AND QQ < AR(2) AND QQ >= AR(3) AND QQ < AR(4) THEN CC = 10
            LINE (QQ * 2, (-SYY1) + 200)-(QQ * 2 + 2, (-SYY2) + 200), CC
            NEXT QQ
            '
            '---------------------------------------------------- 'EC
CHANCALC:
            CHANO = 0
            FOR QQ = 25 TO 150           'From 50 to 300 Hz
            YY1 = FFTOUT(QQ, FFTN)
            YY2 = FFTOUT(QQ + 1, FFTN)
            grad = ABS(YY2 - YY1)
            'LOCATE 10, 18: PRINT grad
            CHANO = grad + CHANO    'EC
            NEXT QQ
            CHANO = 100 * CHANO / MAXVEC
            '-------------------------------------------
            IF FFTN = 1 THEN AR(5) = CHANO
            IF FFTN = 2 THEN AR(6) = CHANO
            IF FFTN = 3 THEN AR(7) = CHANO
            IF DISP3 = 0 THEN CI = FIX(CHANO)
            IF DISP3 = 1 THEN CI = FIX((AR(5) + AR(6) + AR(7)) / 3)     'EC IF DISP3 = 1 AND FFTN < 3 THEN
               FFTN = FFTN + 1
               GOTO DISP3L
            END IF
11240    '----------------------------------- CHANGING TEXT DISPLAY
            IF DISP3 = 1 THEN
               LOCATE 20, 30: COLOR 11, 0
               PRINT "(MEAN of X, Y, Z Indices)"
            END IF
            '
            LOCATE 20, 24: COLOR 14, 0
            PRINT CI; " "
            '---------------------------------- GET USER INPUT
11250    QQ = XKEY
            '---------------------------------- EXIT KEYS
            IF QQ = 13 THEN EXIT SUB
            IF QQ = 3 THEN CLOSE #1, #2, #3: END
```

```
'---------------------------------- SELECT POINT TO ADJUST
IF QQ = ASC("1") THEN ARN = 1: GOTO 11240
IF QQ = ASC("2") THEN ARN = 2: GOTO 11240
IF QQ = ASC("3") THEN ARN = 3: GOTO 11240
IF QQ = ASC("4") THEN ARN = 4: GOTO 11240
GOTO 11250
END SUB

SUB FFTMATH
    ON ERROR GOTO 0
    '--------------------------------- FFT routine
    FFTS = 512
    DIM X1(512): DIM X2(512)
    FOR QQ = 0 TO 511: X1(QQ) = SEGM(QQ): X2(QQ) = 0: NEXT QQ PRINT "PERFORMING FFT.....";
    L = INT(LOG(FFTS) / LOG(2))
    I1 = FFTS / 2: I2 = 1: V = 2 * API / FFTS
    FOR I = 1 TO L: I3 = 0: I4 = I1
     FOR K = 1 TO I2: X = INT(I3 / I1)
       IF K / 20 = FIX(K / 20) THEN PRINT ".";
       Y = 0: N1 = FFTS
       FOR W = 1 TO L
         N1 = N1 / 2: IF X < N1 GOTO 11020
         Y = Y + 2 ^ (W - 1): X = X - N1
11020    NEXT W
         I5 = Y
         C1 = COS(V * I5): C2 = -SIN(V * I5)
         FOR M = I3 TO I4 - 1
           A1 = X1(M): A2 = X2(M)
           B1 = C1 * X1(M + I1) - C2 * X2(M + I1)
           B2 = C2 * X1(M + I1) + C1 * X2(M + I1)
           X1(M) = A1 + B1: X2(M) = A2 + B2
           X1(M + I1) = A1 - B1: X2(M + I1) = A2 - B2: NEXT M
         I3 = I3 + 2 * I1: I4 = I4 + 2 * I1: NEXT K
       I1 = I1 / 2: I2 = I2 * 2: NEXT I
    X1(0) = X1(0) / FFTS: X2(0) = X2(0) / FFTS
    '--------------------------------- adjust data
    FOR Z = 1 TO FFTS - 1: X1(Z) = 2 * X1(Z) / FFTS: X2(Z) = -2 * X2(Z) / FFTS: NEXT Z
    '--------------------------------- MAKE OUTPUT ARRAY
    MAXVEC = 0
    FOR U = 0 TO FFTS / 2 '----- TWO MAKES 512Hz  FOUR MAKES 256Hz  SCALE
      X = U: Y = 0: N1 = FFTS
      FOR W = 1 TO L
        N1 = N1 / 2: IF X < N1 GOTO 11100
        Y = Y + 2 ^ (W - 1): X = X - N1
11100   NEXT W
      FFTOUT(U, FFTN) = SQR(X1(Y) * X1(Y) + X2(Y) * X2(Y))
       IF PWR = 0 THEN FFTOUT(U, FFTN) = FFTOUT(U, FFTN) ^ 2
       IF FFTOUT(U, FFTN) > MAXVEC THEN MAXVEC = FFTOUT(U, FFTN)
      NEXT U
END SUB
```

A-7

```
SUB FFTOPT
    CLS
SEL1: '-------------------------------- FFT MAIN ROUTINE
    COLOR 11, 0: LOCATE 2, 1
    PRINT "Highlighted selections in"
    COLOR 14, 0: LOCATE 2, 27: PRINT "yellow"
    COLOR 11, 0: LOCATE 2, 34: PRINT "will specify analysis."
    PRINT
    PRINT "Change selections by pressing the corresponding letter."
    PRINT
    PRINT
    LOCATE 6, 1: COLOR 15, 0: PRINT "Window functions:"
    IF WIN = 0 THEN COLOR 14, 0 ELSE COLOR 7, 0
    LOCATE 7, 1: PRINT "<B> Blackman-Harris"
    IF WIN = 1 THEN COLOR 14, 0 ELSE COLOR 7, 0
    LOCATE 8, 1: PRINT "<H> Hanning"
    IF WIN = 2 THEN COLOR 14, 0 ELSE COLOR 7, 0
    LOCATE 9, 1: PRINT "<R> Rectangle"
     LOCATE 6, 30: COLOR 15, 0: PRINT "Lead:"
    IF LL = 1 THEN COLOR 14, 0 ELSE COLOR 7, 0
    LOCATE 7, 30: PRINT "<X> X Lead"
    IF LL = 2 THEN COLOR 14, 0 ELSE COLOR 7, 0
    LOCATE 8, 30: PRINT "<Y> Y Lead"
    IF LL = 3 THEN COLOR 14, 0 ELSE COLOR 7, 0
    LOCATE 9, 30: PRINT "<Z> Z Lead"
    IF LL = 0 THEN COLOR 14, 0 ELSE COLOR 7, 0
    LOCATE 10, 30: PRINT "<C> Composite (X+Y+Z)"
    IF LL = 4 THEN COLOR 14, 0 ELSE COLOR 7, 0
    LOCATE 11, 30: PRINT "<T> Tri (Simultaneous X,Y,Z)"
    LOCATE 6, 50: COLOR 15, 0: PRINT "Graph Scale:"
    IF PWR = 0 THEN COLOR 14, 0 ELSE COLOR 7, 0
    LOCATE 7, 50: PRINT "<P> Power"
    IF PWR = 1 THEN COLOR 14, 0 ELSE COLOR 7, 0
    LOCATE 8, 50: PRINT "<A> Amplitude"
    LOCATE 14, 1: COLOR 15, 0: PRINT "Mean Adjustment:"
    IF DCYN = 1 THEN COLOR 14, 0 ELSE COLOR 7, 0
    LOCATE 15, 1: PRINT "<O> Mean DC = 0"
    IF DCYN = 0 THEN COLOR 14, 0 ELSE COLOR 7, 0
    LOCATE 16, 1: PRINT "<N> Natural Mean"
    LOCATE 14, 30: COLOR 15, 0: PRINT "0 db:"
    IF DB = 0 THEN COLOR 14, 0 ELSE COLOR 7, 0
    LOCATE 15, 30: PRINT "<M> Maxima"
    IF DB = 1 THEN COLOR 14, 0 ELSE COLOR 7, 0
    LOCATE 16, 30: PRINT "<D> True db"
    IF DB = 2 THEN COLOR 14, 0 ELSE COLOR 7, 0
    LOCATE 17, 30: PRINT "<V> u Volts"
    LOCATE 22, 51: COLOR 14, 0: PRINT "<ENTER>"
    LOCATE 22, 59: COLOR 15, 0: PRINT "to Accept."
    QQ = XKEY
    IF QQ = 13 THEN EXIT SUB
    IF QQ = 66 OR QQ = 98 THEN WIN = 0
    IF QQ = 72 OR QQ = 104 THEN WIN = 1
    IF QQ = 82 OR QQ = 114 THEN WIN = 2
    IF QQ = 88 OR QQ = 120 THEN LL = 1
    IF QQ = 89 OR QQ = 121 THEN LL = 2
    IF QQ = 90 OR QQ = 122 THEN LL = 3
    IF QQ = 67 OR QQ = 99 THEN LL = 0
    IF QQ = 84 OR QQ = 116 THEN LL = 4
    IF QQ = 80 OR QQ = 112 THEN PWR = 0
    IF QQ = 65 OR QQ = 97 THEN PWR = 1
    IF QQ = 78 OR QQ = 110 THEN DCYN = 0
    IF QQ = 48 THEN DCYN = 1
    IF QQ = 77 OR QQ = 109 THEN DB = 0
    IF QQ = 68 OR QQ = 100 THEN DB = 1
    IF QQ = 86 OR QQ = 118 THEN DB = 2
    GOTO SEL1
END SUB
```

A-8

```
SUB FFTPEAK
        IF DB = 1 OR DB = 2 THEN MAXVEC = 1
        '---------------------------------- FIND FIXED POINTS
        FIXF(1, FFTN) = 5
        FIXM(1, FFTN) = SCYY * FFTOUT(5, FFTN) / MAXVEC
        FIXF(2, FFTN) = 13
        FIXM(2, FFTN) = SCYY * FFTOUT(13, FFTN) / MAXVEC
        FIXF(3, FFTN) = 20
        FIXM(3, FFTN) = SCYY * FFTOUT(20, FFTN) / MAXVEC
        FIXF(4, FFTN) = 40
        FIXM(4, FFTN) = SCYY * FFTOUT(40, FFTN) / MAXVEC
        '---------------------------------- FIND PEAK POINTS
        OLD = 0: CHK = 0: STP = 0
        FOR QQ = 10 TO 50'------------- 20Hz TO 100Hz
        MMAG = SCYY * FFTOUT(QQ, FFTN) / MAXVEC
        IF OLD < MMAG THEN CHK = CHK + 1: GOTO 11500
        IF CHK < 2 THEN CHK = 0: GOTO 11500
        PEAKF(STP, FFTN) = QQ - 1
        PEAKM(STP, FFTN) = OLD
        CHK = 0
        STP = STP + 1
11500   OLD = MMAG
        NEXT QQ
END SUB

SUB FFTPLOT
11275   '---------------------------------- WAKE UP PLOTTER
        INITPLOT
        '---------------------------------- DISPLAY LAST SCREEN INFO
        CALL CLEARBOT(18, 6)
        PRINT
        IF VAL(INN$(3)) = 1 OR VAL(INN$(3)) = 2 THEN PRINT "Plotting...   Please wait."
        IF VAL(INN$(3)) = 3 THEN PRINT "Plotting to file "; PFN$; "...   Please wait."
        '---------------------------------- PLOT DEMOGRAPHICS
        PLOTDEMO
        '---------------------------------- PLOT SCALE LINES
        POUT$ = "PUSP1IW0,0,10300,6750PA6500,6250PDPR": PLOTDATA (POUT$)
        POUT$ = "-6000,0,0,-6000,PU": PLOTDATA (POUT$)
        '---------------------------------- PLOT AMPLITUDE TICK MARKS
        XDEK = 0: XINC = 0
        POUT$ = "DI0,-1SI.11,.16": PLOTDATA (POUT$)
        IF DB = 2 THEN
         PPW = 1000 / SCY
         POUT$ = "PA6500,6650LB10^" + STR$(3 * PPW) + CHR$(3): PLOTDATA (POUT$)
         ELSE
         POUT$ = "PA6500,6400LB0" + CHR$(3): PLOTDATA (POUT$)
        END IF
11300   XTX = FIX(LOG(20 ^ XDEK * (XINC + 1)) / ADB * SCY)
        IF XTX > 6000 THEN GOTO 11350
        POUT$ = "PA" + STR$(6500 - XTX) + ",6250;XT;": PLOTDATA (POUT$)
        IF XINC < 18 THEN XINC = XINC + 1: GOTO 11300
        XDEK = XDEK + 1: XINC = 0
        IF DB = 2 THEN
         POUT$ = "PA" + STR$(6500 - XDEK * SCY) + ",6650": PLOTDATA (POUT$)
         POUT$ = "LB10^" + STR$(3 * PPW - XDEK) + CHR$(3): PLOTDATA (POUT$)
         ELSE
         POUT$ = "PA" + STR$(6500 - XDEK * SCY) + ",6630": PLOTDATA (POUT$)
         POUT$ = "LB" + STR$(XDEK * -20) + CHR$(3): PLOTDATA (POUT$)
        END IF
        GOTO 11300
```

A-9

```
11350 '-------------------------- PLOT FREQUENCY TICK MARKS
       YDEK = 0: YINC = 1
       POUT$ = "SI.14,.21PA350,6240LB2" + CHR$(3): PLOTDATA (POUT$)
11370  YTY = FIX(LOG((10 ^ YDEK * YINC) / 2) / AE * 2491)
       IF (10 ^ YDEK * YINC) >= 512 THEN GOTO 11420
       POUT$ = "PA500," + STR$(6250 - YTY) + ";YT;": PLOTDATA (POUT$)
       IF YINC < 9 THEN YINC = YINC + 1: GOTO 11370
       YDEK = YDEK + 1: YINC = 1
       POUT$ = "PA350," + STR$(7150 - YDEK * 2491): PLOTDATA (POUT$)
       POUT$ = "LB" + STR$(10 ^ YDEK) + CHR$(3): PLOTDATA (POUT$)
       GOTO 11370
11420  POUT$ = "PA350,400LB500" + CHR$(3): PLOTDATA (POUT$)
       '-------------------------- PLOT TEXT FOR SCALE
       POUT$ = "PUSI.21,.32PA75,4000LB": PLOTDATA (POUT$)
       POUT$ = "Frequency Hz" + CHR$(3): PLOTDATA (POUT$)
       POUT$ = "PUPA5000,6750LB": PLOTDATA (POUT$)
       POUT$ = "A" + CRLF$ + "m" + CRLF$ + "p" + CRLF$: PLOTDATA (POUT$)
       POUT$ = "l" + CRLF$ + "i" + CRLF$ + "t" + CRLF$: PLOTDATA (POUT$)
       POUT$ = "u" + CRLF$ + "d" + CRLF$ + "e" + CRLF$: PLOTDATA (POUT$)
       IF DB = 2 THEN
         POUT$ = " " + CRLF$ + "u" + CRLF$ + "V" + CHR$(3): PLOTDATA (POUT$)
       ELSE
         POUT$ = " " + CRLF$ + "d" + CRLF$ + "b" + CHR$(3): PLOTDATA (POUT$)
       END IF
       POUT$ = "PUSI.14,.21": PLOTDATA (POUT$)
       '-------------------------- PLOT FFT OUTPUT GRAPH
       POUT$ = "PUSP2"
       IF DISP3 = 1 THEN FFTN = 1

PLOT3L: IF DISP3 = 1 AND FFTN = 1 THEN POUT$ = "PUSP1"
       IF DISP3 = 1 AND FFTN = 2 THEN POUT$ = "PUSP2"
       IF DISP3 = 1 AND FFTN = 3 THEN POUT$ = "PUSP3"
       PLOTDATA (POUT$)

XAA = FIX(LOG(SCYY * FFTOUT(1, FFTN) / MAXVEC) / AE * SCY)
       POUT$ = "PA500,6250PUPR": PLOTDATA (POUT$)
       POUT$ = STR$(XAA) + ",0PD": PLOTDATA (POUT$)
       OLDX = XAA
       OLDY = 0
       FOR QQ = 2 TO 256
         YY = FIX(LOG(SCYY * FFTOUT(QQ, FFTN) / MAXVEC) / AE * SCY)
         XX = FIX(LOG(QQ + 1) / AE * 2491)
         IF QQ = AR(1) THEN POUT$ = "PUXTYTPDPR": PLOTDATA (POUT$)
         IF QQ = AR(2) THEN POUT$ = "PUXTYTPDPR": PLOTDATA (POUT$)
         IF QQ = AR(3) THEN POUT$ = "PUXTYTPDPR": PLOTDATA (POUT$)
         IF QQ = AR(4) THEN POUT$ = "PUXTYTPDPR": PLOTDATA (POUT$)
         IF YY < 0 THEN YY = 0
         IF XX < 0 THEN XX = 0
         IF YY > 6000 THEN YY = 6000
         IF XX > 6000 THEN XX = 6000
         POUT$ = STR$(YY - OLDX) + "," + STR$(-(XX - OLDY)) + ","
         PLOTDATA (POUT$)
         OLDX = YY
         OLDY = XX
       NEXT QQ

IF DISP3 = 1 AND FFTN < 3 THEN
         FFTN = FFTN + 1
         GOTO PLOT3L
       END IF
```

```
'----------------------------------- PLOT CHAN Index
IF DISP3 = 1 THEN
 POUT$ = "PUSP2PA6500,2900LBMean" + CHR$(3): PLOTDATA (POUT$)
END IF
'
POUT$ = "PUPA6500,2500LB": PLOTDATA (POUT$)
POUT$ = "CHAN Index: " + STR$(CI) + CRLF$: PLOTDATA (POUT$)
'POUT$ = "Numerator of " + STR$(AR(3) * 2): PLOTDATA (POUT$)
POUT$ = STR$(AR(3) * 2) + " Hz to " + STR$(AR(4) * 2) + " Hz" + CRLF$ + CHR$(3): PLOTDATA
(POUT$)
'POUT$ = "Denominator of " + STR$(AR(1) * 2): PLOTDATA (POUT$)
'POUT$ = " Hz to " + STR$(AR(2) * 2) + " Hz" + CHR$(3): PLOTDATA (POUT$)
'---------------------------------- PLOT FIXED POINT DATA
IF PWR <> 0 OR DCYN <> 0 OR DB <> 0 THEN GOTO NOPT
'
POUT$ = "PUSP1PA4500,6000LB": PLOTDATA (POUT$)
POUT$ = "Fixed frequency points." + CRLF$: PLOTDATA (POUT$)
POUT$ = "Freq   Rel db   Mag Ratio" + CHR$(3): PLOTDATA (POUT$)

POUT$ = "SP2PA4100,6000LB": PLOTDATA (POUT$)
FOR QQ = 1 TO 4
POUT$ = STR$(FIXF(QQ, FFTN) * 2) + CRLF$: PLOTDATA (POUT$)
NEXT QQ
'
POUT$ = CHR$(3) + "PA4100,5250LB": PLOTDATA (POUT$)
FOR QQ = 1 TO 4
POUT$ = STR$(FIX(((LOG(FIXM(QQ, FFTN)) / AE) - 1000 / SCY * 3) * 20)) + CRLF$: PLOTDATA
(POUT$)
NEXT QQ
'
POUT$ = CHR$(3) + "PA4100,4500LB": PLOTDATA (POUT$)
FOR QQ = 1 TO 4
POUT$ = STR$(FIX(FIXM(QQ, FFTN) * 100000 / SCYY * 1000) / 1000) + CRLF$: PLOTDATA
(POUT$)
NEXT QQ
'
POUT$ = CHR$(3): PLOTDATA (POUT$)
'---------------------------------- PLOT PEAKS POINT DATA
POUT$ = "PUSP1PA3000,6000LB": PLOTDATA (POUT$)
POUT$ = "Magnitude of detected peaks." + CRLF$: PLOTDATA (POUT$)
POUT$ = "Freq   Rel db   Mag Ratio" + CHR$(3): PLOTDATA (POUT$)
POUT$ = "SP2PA2600,6000LB": PLOTDATA (POUT$)
FOR QQ = 0 TO 15
IF PEAKF(QQ, FFTN) = 0 THEN GOTO 12000
POUT$ = STR$(PEAKF(QQ, FFTN) * 2) + CRLF$: PLOTDATA (POUT$)
12000 NEXT QQ
'
POUT$ = CHR$(3) + "PA2600,5250LB": PLOTDATA (POUT$)
FOR QQ = 0 TO 15
IF PEAKF(QQ, FFTN) = 0 THEN GOTO 12100
POUT$ = STR$(FIX(((LOG(PEAKM(QQ, FFTN)) / AE) - 1000 / SCY * 3) * 20)) + CRLF$: PLOTDATA
(POUT$)
12100 NEXT QQ
'
POUT$ = CHR$(3) + "PA2600,4500LB": PLOTDATA (POUT$)
FOR QQ = 0 TO 15
IF PEAKF(QQ, FFTN) = 0 THEN GOTO 12200
POUT$ = STR$(FIX(PEAKM(QQ, FFTN) * 100000 / SCYY * 1000) / 1000) + CRLF$: PLOTDATA
(POUT$)
12200 NEXT QQ
'
POUT$ = CHR$(3): PLOTDATA (POUT$)
```

A-11

```
NOPT:   '------------------------------ PLOT INPUT TRACE
        POUT$ = "PUSP1"
        IF DISP3 = 1 THEN FFTN = 1

PL3L:   IF DISP3 = 1 AND FFTN = 1 THEN POUT$ = "PUSP1"
        IF DISP3 = 1 AND FFTN = 2 THEN POUT$ = "PUSP2"
        IF DISP3 = 1 AND FFTN = 3 THEN POUT$ = "PUSP3"
        PLOTDATA (POUT$)

IF DISP3 = 1 THEN FOR QQ = 1 TO 799: LEAD(QQ) = XYZ(QQ * 3 + FFTN - 1): NEXT QQ
        POUT$ = "PA9000,6750PDPR": PLOTDATA (POUT$)
        L = 0
        FOR J = 0 TO 799
          M = FIX(LEAD(J) * 5 / 64)
          IF J = BW THEN POUT$ = "PUXTYTSP2PDPR": PLOTDATA (POUT$)

IF J = EW THEN
              POUT$ = "PUSP1"
              IF DISP3 = 1 AND FFTN = 1 THEN POUT$ = "PUSP1"
              IF DISP3 = 1 AND FFTN = 2 THEN POUT$ = "PUSP2"
              IF DISP3 = 1 AND FFTN = 3 THEN POUT$ = "PUSP3"
              PLOTDATA (POUT$)

POUT$ = "XTYTPDPR": PLOTDATA (POUT$)
          END IF
          POUT$ = STR$(M - L) + "," + STR$(-8) + ",": PLOTDATA (POUT$)
          L = M
        NEXT J

IF DISP3 = 1 AND FFTN < 3 THEN
          FFTN = FFTN + 1
          GOTO PL3L:
        END IF
        '------------------------------ PLOT OPTIONS DATA
        IF DISP3 = 1 THEN LL$ = "X,Y,Z Mean"

POUT$ = "PUSP2PA7500,6000LB": PLOTDATA (POUT$)
        POUT$ = "Window Begins at" + STR$(BW): PLOTDATA (POUT$)
        POUT$ = "mS and Ends at" + STR$(EW): PLOTDATA (POUT$)
        POUT$ = "mS, with a Delta of" + STR$(DELTA) + "mS" + CRLF$: PLOTDATA (POUT$)
        POUT$ = "Patient Lead   : " + LL$ + CRLF$: PLOTDATA (POUT$)
        POUT$ = "Window Type    : " + WIN$ + CRLF$: PLOTDATA (POUT$)
        POUT$ = "Max uV in Window : " + STR$(FIX(AMAXV * 5 / 64 * 10) / 10) + " uV" + CRLF$: PLOTDATA
        (POUT$)
        'POUT$ = "Windowed Res.  : " + STR$(FIX(10240 / ((EW - BW) * FRWF)) / 10) + " Hz" + CRLF$:
        PLOTDATA (POUT$)
        'POUT$ = "Freq. Resolution : " + STR$(FIX(512 / DELTA * 20) / 10) + " Hz" + CRLF$: PLOTDATA
        (POUT$)
        POUT$ = "Magnitude Scale  : " + PWR$ + CHR$(3): PLOTDATA (POUT$)
30000   '------------------------------ PROGRAM END
        POUT$ = "PUIWPA0,0SP;": PLOTDATA (POUT$) ' PUT PLOTTER TO BED
        CLOSE #1
END SUB
```

```
SUB FFTPREP
    DIM TEMP(512)
    '--------------------------------- VOLTAGE OR POWER
    IF PWR = 1 THEN
        '--------------
        PWR$ = "AMPLITUDE"
        SCY = 1000        ' Scale to 1"
        SCYY = 1000000    '
    ELSE
        '--------------
        PWR$ = "POWER"
        SCY = 500         ' Scale to .5"
        SCYY = 1E+12      '
    END IF
    '--------------------------------- LEAD SELECTION
    IF LL = 0 THEN LL$ = "Composite (X+Y+Z)"
    IF LL = 1 THEN LL$ = "X-Lead"
    IF LL = 2 THEN LL$ = "Y-Lead"
    IF LL = 3 THEN LL$ = "Z-Lead"
    PRINT "Preparing "; LL$; " for Fourier Transform."
    AMAXV = 0
    FOR QQ = 0 TO 799
        IF LL = 0 THEN LEAD(QQ) = (XYZ(QQ * 3) + XYZ(QQ * 3 + 1) + XYZ(QQ * 3 + 2)) / 3 '----composite lead
        IF LL > 0 THEN LEAD(QQ) = XYZ(QQ * 3 + LL - 1)'------ selected lead
    NEXT QQ
    '---------------------------------------#EC1
    PRINT "Calculating Acceleration Spectrum. Please wait."
    FOR QQ = 0 TO 798
        DIFF(QQ) = LEAD(QQ + 1) - LEAD(QQ)    '1st. Derivative
    NEXT QQ
    DIFF(799) = DIFF(798)

FOR QQ = 0 TO 798                         '2nd. Derivative
        ACCEL(QQ) = DIFF(QQ + 1) - DIFF(QQ)
    NEXT QQ
    ACCEL(799) = ACCEL(798)

'--------------------------------- TRANSFER DATA INTO SEGM(N)
    '-----SHIFT DATA INTO BEGINNING OF ARRAY, FILL REST WITH NULLS
    FOR QQ = 0 TO DELTA
        SEGM(QQ) = ACCEL(QQ + BW)
        TEMP(QQ) = SEGM(QQ)
        WIND(QQ) = 1
    NEXT QQ

FOR QQ = DELTA TO 512
        SEGM(QQ) = 0
        TEMP(QQ) = 0
        WIND(QQ) = 0
    NEXT QQ
WIN: '--------------------------------- WINDOW FUNCTION
    IF WIN = 0 THEN GOTO BH
    IF WIN = 1 THEN GOTO HAN
    IF WIN = 2 THEN GOTO NONE
BH:  '--------------
    WIN$ = "Blackman-Harris"
    PRINT WIN$; " Window Function....";
    B = 2 * API / DELTA
    FOR QQ = 0 TO DELTA
        WIND(QQ) = WIND(QQ) * (.35875 - .48829 * COS(B * QQ) + .14128 * COS(B * 2 * QQ) - .01168 * COS(B * 3 * QQ))
        IF QQ / 20 = FIX(QQ / 20) THEN PRINT ".";
    NEXT QQ
    GOTO WDONE
```

```
HAN:    '--------------------------
        WIN$ = "Hanning"
        PRINT WIN$; " Window Function....";
        FOR QQ = 0 TO DELTA
           WIND(QQ) = WIND(QQ) * .5 * (1 - COS(2 * (QQ - 1) * API / DELTA))
           IF QQ / 20 = FIX(QQ / 20) THEN PRINT ".";
        NEXT QQ
        GOTO WDONE
NONE:   '--------------------------
        WIN$ = "Rectangle"
        PRINT WIN$; " Window Function....";
        FOR QQ = 0 TO DELTA
           WIND(QQ) = WIND(QQ)
           IF QQ / 20 = FIX(QQ / 20) THEN PRINT ".";
        NEXT QQ
WDONE:  '------------------------------- DC BIAS ADJUST
        IF DCYN = 1 THEN
           PRINT
           PRINT "REMOVING DC-BIAS (MEAN=0)...";
           TOTS = 0: TOTW = 0
           FOR QQ = 0 TO DELTA
                SEGM(QQ) = SEGM(QQ) * WIND(QQ)
                TOTS = TOTS + SEGM(QQ)
                TOTW = TOTW + WIND(QQ)
                IF QQ / 20 = FIX(QQ / 20) THEN PRINT ".";
           NEXT QQ
           DCOFF = TOTS / TOTW
           FOR QQ = 0 TO DELTA
                SEGM(QQ) = (TEMP(QQ) - DCOFF) * WIND(QQ) '- MEAN=0 WINDOW
                IF QQ / 20 = FIX(QQ / 20) THEN PRINT ".";
           NEXT QQ
        ELSE
           FOR QQ = 0 TO DELTA
                SEGM(QQ) = SEGM(QQ) * WIND(QQ) '---------- NATURAL WINDOW
                IF QQ / 20 = FIX(QQ / 20) THEN PRINT ".";
           NEXT QQ
        END IF
        PRINT
        '------------------------------- FIND MAX VOLTAGE
        FOR QQ = 0 TO DELTA
           IF AMAXV < ABS(SEGM(QQ)) THEN AMAXV = ABS(SEGM(QQ))
        NEXT QQ
        '------------------------------- SCALE POINTS MAX TO 1
        FOR QQ = 0 TO DELTA
           SEGM(QQ) = SEGM(QQ) / AMAXV
        NEXT QQ
END SUB SUB FFTSEG
BIGSM:  '------------------------------- FFT MAIN ROUTINE
        SELWIND'----------------- get window of data
        CALL CLEARBOT(18, 6)'--------- clear bottom
        IF DELTA >= 20 AND DELTA < 512 THEN EXIT SUB
           BEEP
           PRINT "Poor point selection...... Window DELTA should be >= 20mS"
           PRINT "               OR... Window DELTA should be < 512mS"
           PRINT "Press any key to continue.": QQ = XKEY: GOTO BIGSM
END SUB
```

```
' ACCELCOM.BAS  -  COMPANION MODULE FOR ACCELFFT
'
' Arrhythmia Research Technology Inc.
' 5910 Courtyard Drive
' Suite 300
' Austin, Texas
' 78731
'
' Copyright ART, 1988, 1989. All rights reserved.

'------------------------------ COMMON MODULE SUBROUTINES
        DECLARE SUB CHKCRT ()
        DECLARE SUB CLEARBOT (BLN, NLN)
        DECLARE SUB CLINE ()
        DECLARE SUB GETFDATA ()
        DECLARE SUB INITPLOT ()
        DECLARE SUB PLOTDATA (POUT$)
        DECLARE SUB PLOTDEMO ()
        DECLARE SUB RAWDRAW ()
        DECLARE SUB SELWIND ()
        DECLARE SUB SHOWDATA ()
'------------------------------ COMMON MODULE FUNCTIONS
        DECLARE FUNCTION XKEY! ()
'------------------------------ COMMON VARIABLES
        COMMON SHARED /PROGID/ PROG$, VER$
        COMMON SHARED /ARRAYS/ INN$(), XYZ()
        COMMON SHARED /FILENAMES/ IFILE$, PFN$
        COMMON SHARED /DEMO/ ECGLEN, SID1$, STD1$, STU1$, STS1$, SSW1$
        COMMON SHARED /DEMO1/ ECGCK, STU$, STS$, SEQ, SNA$, SID$, SDA$, STI$
        COMMON SHARED /DEMO2/ SAG$, SEX$, SHT$, SWT$, SRA$, SM1$, SM2$, SSBP$
        COMMON SHARED /DEMO3/ SDBP$, SOP$, SC$, QRSON, QRSOFF
        COMMON SHARED /CONSTANTS/ ESC$, CRLF$, API, AE, ADB
        COMMON SHARED /SELWIND/ BW, EW, DELTA, FRWF
        COMMON SHARED /FFTVAR/ WIN, LL, PWR, DCYN
'------------------------------ COMMON MODULE VARIABLES
        COMMON SHARED /EETRAP/ AOK
'
        ON ERROR GOTO ETRAP
        END

ETRAP: '------------------------------ TRAP BI-PASS
        '---- FILE DOES NOT EXIST, ALL CLEAR, GO TO IT
        IF ERL = 116 AND (ERR = 53 OR ERR = 64) THEN AOK = 1: RESUME NEXT
        '---- FILE DOES NOT EXIST, OPEN IT, WRITE TO IT
        IF ERL = 119 AND (ERR = 53 OR ERR = 64) THEN RESUME
        '----------------------
        '---- FILE DOES NOT EXIST, OPEN IT, WRITE TO IT
        IF ERL = 211 AND (ERR = 53 OR ERR = 64) THEN
            PRINT "Patient data directory probably incorrect."
            GOTO KABOOM1
        END IF
        '---- FILE DOES NOT EXIST, OPEN IT, WRITE TO IT
        IF ERL = 212 AND (ERR = 53 OR ERR = 64) THEN
            PRINT "Patient file not found."
            GOTO KABOOM1
        END IF
        '----------------------
        IF ERL = 311 AND ERR = 5 THEN
            PRINT "EGA DISPLAY NOT PRESENT OR IMPROPERLY CONFIGURED."
            GOTO KABOOM1
        END IF
        IF ERL = 312 AND ERR = 5 THEN
            PRINT "NO VGA DISPLAY PRESENT - EGA MODE"
            RESUME NEXT
        END IF
```

```
'------------------------------ ERROR TRAP
        BEEP: CLS
        IF ERR = 5 THEN PRINT "Display Board Problems   ": GOTO KABOOM
        IF ERR = 24 THEN PRINT "Device Timeout          ": GOTO KABOOM
        IF ERR = 25 THEN PRINT "Serial Port Problems    ": GOTO KABOOM
        IF ERR = 52 OR ERR = 63 THEN PRINT "Bad Filename   ": GOTO KABOOM
        IF ERR = 53 OR ERR = 64 THEN PRINT "File Not Found ": GOTO KABOOM
        IF ERR = 57 THEN PRINT "General I/O Error       ": GOTO KABOOM
        IF ERR = 58 THEN PRINT "File Allready Exists    ": GOTO KABOOM
        IF ERR = 68 THEN PRINT "Serial Port Problems    ": GOTO KABOOM
        IF ERR = 71 THEN PRINT "Selected Drive Not Ready ": GOTO KABOOM
        IF ERR = 72 THEN PRINT "Disk Media Error        ": GOTO KABOOM
        IF ERR = 75 OR ERR = 76 THEN PRINT "Path Problems  ": GOTO KABOOM
        PRINT "Undefined error number "; ERR;
KABOOM:
        PRINT " on line "; ERL; ".  Abnormal End."
KABOOM1:
        PRINT
        PRINT "ANY KEY TO EXIT"
        BEEP
        QQ = XKEY
        CLOSE #1, #2, #3
        END TTRAP: '------------------------------ Timeout Trap
        BEEP: CALL CLEARBOT(18, 6): PRINT
        PRINT "Serial link to Plotter not responding."
        PRINT
        PRINT "Check if plotter is ON and cables are mated."
        PRINT
        PRINT "Tap <ENTER> to retry."
        PRINT "Tap <ESC> to ABORT."
        QQ = XKEY
        IF QQ = 13 THEN RETURN
        GOTO TTRAP
        END SUB CHKCRT
        ON ERROR GOTO ETRAP
311     SCREEN 9, 0, 0, 0: XGA = 9
        IF INN$(4) = "VGA" AND INN$(5) = "FFTPLUS" THEN GOTO 312
        EXIT SUB
312     SCREEN 13, 0, 0, 0: XGA = 13 '------ GOTO NEXT HIGHEST
        SCREEN 9, 0, 0, 0
END SUB SUB CLEARBOT (BLN, NLN) '------------------ clear bottom text
        ON ERROR GOTO ETRAP
        LOCATE BLN, 1
        FOR PPP = 1 TO NLN
        PRINT "                                                         "
        NEXT PPP
        LOCATE BLN, 1
END SUB
```

```
SUB CLINE
    ON ERROR GOTO ETRAP
    '----------------------- BREAK DOWN COMMAND$
    'INN$(1) = INPUT FILE NAME
    'INN$(2) = PATH TO FILES
    'INN$(3) = HARDCOPY DEVICE/PORT
    'INN$(4-9) = N/U
    '
    C$ = COMMAND$
    PP = 1
    FOR INX = 1 TO LEN(C$)
    IF MID$(C$, INX, 1) = " " THEN PP = PP + 1: GOTO NADA
    INN$(PP) = INN$(PP) + MID$(C$, INX, 1)
NADA:   NEXT INX
    '
    IF VAL(INN$(3)) <> 3 AND VAL(INN$(3)) <> 1 THEN INN$(3) = CHR$(48 + 2)
END SUB

SUB CPRT
    ON ERROR GOTO ETRAP
    CLS
    LOCATE 9, 31: COLOR 9, 0: PRINT PROG$; " --- Ver. "; VER$
    LOCATE 12, 24: COLOR 15, 0: PRINT "Arrhythmia Research Technology Inc."
    LOCATE 13, 39: COLOR 15, 0: PRINT "ART"
    LOCATE 16, 32: COLOR 12, 0:
    FOR NN = 1 TO 500: NEXT NN
    FOR NN = 1 TO 320 STEP 3
    VIEW (NN, NN * .54687)-(639 - NN, 349 - NN * .54687), , 1
    NEXT NN
    VIEW (0, 0)-(639, 349), 0, 0
END SUB SUB GETFDATA
    ON ERROR GOTO ETRAP
TOP: '----------------------------- SHOW ALL FILES / SELECT
    IF INN$(1) = "TUTOR.R99" THEN GOTO TUTOR '--- TUTOR / BI-PASS FILE
    '
    IF INN$(1) = "" THEN '---------------- NO FILENAME ON COMMAND
    ENV$ = ENVIRON$("ART") '-------------- GET / ADJUST ENVIRONMENT
NEW:    IF ENV$ = "" THEN ENV$ = "."
    CLS
    COLOR 11, 0
    PRINT "Patient file records on the default drive ";
    COLOR 15, 0
    PRINT ENV$
    COLOR 3, 0
    PRINT "Default executables directory is ";
    COLOR 15, 0
211 FILES ENV$ + "\*.r*"
    PRINT : PRINT : COLOR 11, 0
    PRINT : PRINT : PRINT : PRINT "Type File Name to Process (e.g. LP.R00),"
    PRINT "<*> to Set Drive / Directory,"
    PRINT "<?> for TUTOR / Waveform Generator,"
    PRINT "<CTRL> <C> to ABORT or,"
    INPUT "<ENTER> to Relist.          "; IFILE$
    PRINT : PRINT
    IF IFILE$ = "*" THEN
        PRINT
        INPUT "New drive\directory = "; ENV$
        GOTO NEW
    END IF
```

```
          IF IFILE$ = "?" THEN INN$(1) = "TUTOR.R99": GOTO TUTOR
          IF IFILE$ = "" THEN GOTO TOP
          INN$(1) = IFILE$: INN$(2) = ENV$ + "\"
       END IF

'------------------------------- QUALIFY/ADJUST FILE NAME
       DOT = INSTR(INN$(1), ".")
       IF DOT = 0 THEN INN$(1) = INN$(1) + ".R00"
       IF LEN(INN$(1)) < DOT + 1 THEN INN$(1) = INN$(1) + "R00"
       IFILE$ = INN$(2) + INN$(1)
       '------------------------------- OPEN FILENAME
       CLS : PRINT "Opening File "; IFILE$; " for Input": PRINT
212    OPEN IFILE$ FOR INPUT AS #2
213    CLOSE #2
214    OPEN IFILE$ FOR RANDOM AS #2
215    FIELD #2, 128 AS BYTE$
       '------------------------------- GET 1ST FIELD / FILE HIRES?
       GET #2
       IF (CVI(MID$(BYTE$, 3, 1) + " ") AND 8) THEN GOTO HREKG
       BEEP
       PRINT
       PRINT "WARNING:  WRONG FILE FORMAT !"
       PRINT
       CLOSE #1, #2, #3
       END
HREKG: '------------------------------- WORK WITH DATA / 1200 INFO
       ECGLEN = CVI(MID$(BYTE$, 2, 1) + MID$(BYTE$, 1, 1))    ' ECG LENGTH
       SID1$ = MID$(BYTE$, 4, 12)         ' ID # 1st block
       STD1$ = MID$(BYTE$, 16, 10)        ' Time
       STU1$ = MID$(BYTE$, 26, 4)         ' UNIT #
       STS1$ = MID$(BYTE$, 30, 4)         ' SITE #
       SSW1$ = MID$(BYTE$, 34, 4)         ' 1200 SOFTWARE VER
       '------------------------------- GET 2ND FIELD / DEMOGRAPHICS
       GET #2
       ECGCK = CVI(MID$(BYTE$, 2, 1) + MID$(BYTE$, 1, 1))' RECORD CHECK CODE
       STU$ = MID$(BYTE$, 3, 4)           ' 1200 unit code
       STS$ = MID$(BYTE$, 7, 4)           ' 1200 site code
       SEQ = CVI(MID$(BYTE$, 12, 1) + MID$(BYTE$, 11, 1))   ' ???
       SNA$ = MID$(BYTE$, 13, 21)         ' name
       SID$ = MID$(BYTE$, 34, 13)         ' id
       SDA$ = MID$(BYTE$, 47, 8)          ' date
       STI$ = MID$(BYTE$, 56, 5)          ' time
       SAG$ = MID$(BYTE$, 62, 3)          ' age
       SEX = ASC(MID$(BYTE$, 66, 1))      ' gender
         IF SEX = 0 THEN SEX$ = "Male" ELSE SEX$ = "Female"
       SHT$ = MID$(BYTE$, 67, 4)          ' height
       SWT$ = MID$(BYTE$, 71, 4)          ' weight
       RACE = ASC(MID$(BYTE$, 75, 1))     ' race
         IF RACE = 0 THEN SRA$ = "Caucasian"
         IF RACE = 1 THEN SRA$ = "Black"
         IF RACE = 2 THEN SRA$ = "Hispanic"
         IF RACE = 3 THEN SRA$ = "Oriental"
       MED1 = ASC(MID$(BYTE$, 76, 1))     ' medication 1
         IF MED1 = 1 THEN SM1$ = "Digitalis"
         IF MED1 = 2 THEN SM1$ = "Beta Blocker"
         IF MED1 = 3 THEN SM1$ = "Quinidine/Norpace"
         IF MED1 = 4 THEN SM1$ = "Diuretic"
         IF MED1 = 5 THEN SM1$ = "Calcium Antagonist"
         IF MED1 = 6 THEN SM1$ = "Proc/Lido/Tocainide"
         IF MED1 = 7 THEN SM1$ = "Other Antiarrhytmic"
         IF MED1 = 8 THEN SM1$ = "Psychotropic"
         IF MED1 = 9 THEN SM1$ = "Unknown"
       MED2 = ASC(MID$(BYTE$, 77, 1))     ' medication 2
         IF MED2 = 1 THEN SM2$ = "Digitalis"
         IF MED2 = 2 THEN SM2$ = "Beta Blocker"
         IF MED2 = 3 THEN SM2$ = "Quinidine/Norpace"
```

```
            IF MED2 = 4 THEN SM2$ = "Diuretic"
            IF MED2 = 5 THEN SM2$ = "Calcium Antagonist"
            IF MED2 = 6 THEN SM2$ = "Proc/Lido/Tocainide"
            IF MED2 = 7 THEN SM2$ = "Other Antiarrhytmic"
            IF MED2 = 8 THEN SM2$ = "Psychotropic"
            IF MED2 = 9 THEN SM2$ = "Unknown"
            SSBP$ = MID$(BYTE$, 78, 3)         ' sys bp
            SDBP$ = MID$(BYTE$, 82, 4)         ' dia bp
            SOP$ = MID$(BYTE$, 86, 6)          ' option / location?
            SC$ = STR$(CVI(MID$(BYTE$, 93, 1) + MID$(BYTE$, 92, 1)))  ' cycles
            QRSON = CVI(MID$(BYTE$, 95, 1) + MID$(BYTE$, 94, 1))      ' qrson
            QRSOFF = CVI(MID$(BYTE$, 97, 1) + MID$(BYTE$, 96, 1))     ' qrsoff
            PTR = 98                           ' POINTER TO GET REST OF FILE
            SHOWDATA
            '--------------------------- GET X,Y,Z DATA
            FOR LD = 0 TO 2
            J = LD
              WHILE J < 2400
              IF PTR < 128 THEN
                IY = CVI(MID$(BYTE$, PTR + 1, 1) + MID$(BYTE$, PTR, 1))
                PTR = PTR + 2
                GOTO 5810
              END IF
              IF PTR = 129 THEN GET #2: PTR = 1
                MSB$ = MID$(BYTE$, PTR, 1): PTR = PTR + 1
                    IF PTR = 129 THEN GET #2: PTR = 1
                LSB$ = MID$(BYTE$, PTR, 1): PTR = PTR + 1
                IY = CVI(LSB$ + MSB$): PRINT ".";
5810          XYZ(J) = IY: IF (J > 2) THEN XYZ(J) = XYZ(J - 3) + XYZ(J)
              J = J + 3
              WEND
              XYZ0 = XYZ(3 * QRSON + LD): J = J - 3
              WHILE J >= 0
                XYZ(J) = XYZ(J) - XYZ0
                J = J - 3
              WEND
            NEXT LD
            CLOSE #2
            COLOR 15, 0
            '--------------------------- #ec WAIT FOR ANY KEYSTROKE
            LOCATE 24, 40
            PRINT "<PRESS ANY KEY TO CONTINUE>"
            QQ = XKEY
EXIT SUB TUTOR:  '--------------------------- Sine Wave Generator
            CLS
            LOCATE 1, 1
            COLOR 10, 1: PRINT "Tutor ";
            COLOR 14, 1: PRINT "/ Sine Wave Generator "; ""
            COLOR 12, 1: LOCATE 3, 1
            PRINT "You can create sine waves to analyze rather than complex ECG's."
            PRINT "From a known - simple waveform - that you specify, you can"
            PRINT "experiment, interact with and learn "; PROG$; "."
            COLOR 14, 1: LOCATE 7, 1
            PRINT "Please specify the frequency and amplitude for three leads. (X,Y & Z)"
            COLOR 15, 1: LOCATE 10, 1
            FOR L = 0 TO 2
              IF L = 0 THEN PRINT "Create a X Lead"
              IF L = 1 THEN PRINT "Create a Y Lead"
              IF L = 2 THEN PRINT "Create a Z Lead"
AMPL:       INPUT "Frequency in Hz <.1 to 250, ENTER to bypass>"; FQ
              IF FQ = 0 THEN GOTO BYPASS
              IF FQ < .1 OR FQ > 250 THEN GOTO AMPL
              IF L = 0 THEN SM1$ = "XF=" + STR$(FQ)
              IF L = 1 THEN SM2$ = "YF=" + STR$(FQ)
```

A-19

```
            IF L = 2 THEN SSBP$ = "ZF=" + STR$(FQ)
            FQ = FIX(1000 / FQ)
FREQ:   INPUT "Amplitude in uV <.001 to 2000>"; UV
            IF UV < .001 OR UV > 2000 THEN GOTO FREQ
            IF L = 0 THEN SM1$ = SM1$ + "  XA=" + STR$(UV)
            IF L = 1 THEN SM2$ = SM2$ + "  YA=" + STR$(UV)
            IF L = 2 THEN SSBP$ = SSBP$ + "  ZA=" + STR$(UV)
            UV = UV * 12.8
            FOR Z = 0 TO 799 STEP FQ
              FOR F = 0 TO FQ - 1
                IF Z + F > 799 GOTO FULL
                XYZ((Z + F) * 3 + L) = SIN(2 * API * F / FQ) * UV
FULL:       NEXT F: PRINT ".";
            NEXT Z
BYPASS: PRINT : NEXT L
            QRSON = 200: QRSOFF = 600: SNA$ = "Tutor"
            COLOR 15, 0
END SUB SUB INITPLOT
            ON ERROR GOTO ETRAP
OUTOPT: '-------------------------------- LAST CHANCE COM/FILE/PAPER
            CALL CLEARBOT(18, 6)
            LOCATE 19, 7: COLOR 11, 0
            PRINT "Output data to:";
            IF VAL(INN$(3)) = 1 THEN COLOR 11, 0 ELSE COLOR 15, 0
            PRINT TAB(20); "Plotter - COM1:   <1>   (Is paper loaded?)"
            IF VAL(INN$(3)) = 2 THEN COLOR 11, 0 ELSE COLOR 15, 0
            PRINT TAB(20); "Plotter - COM2:   <2>   (Is paper loaded?)"
            IF VAL(INN$(3)) = 3 THEN COLOR 11, 0 ELSE COLOR 15, 0
            PRINT TAB(20); "Plot File (Laser)  <3>"
            COLOR 15, 0
            PRINT TAB(20); "Abort Plot       <ESC>"
            NPORT = XKEY
            IF NPORT = 13 THEN GOTO OUTDEV
            IF NPORT < 49 OR NPORT > 51 THEN BEEP: GOTO OUTOPT
            INN$(3) = CHR$(NPORT)
OUTDEV: '-------------------------------- INITIALIZE COM PORT / FILE
            IF VAL(INN$(3)) = 1 THEN GOTO OUT1
            IF VAL(INN$(3)) = 3 THEN GOTO OUTP
            OPEN "COM2:9600,N,8,1,CS,DS,CD" FOR RANDOM AS #1: GOTO INITPL
OUT1:   OPEN "COM1:9600,N,8,1,CS,DS,CD" FOR RANDOM AS #1: GOTO INITPL
OUTP:   '--------------------------------- Output to a file
            '----- The error trap (ETRAP) is an important part of this routine
            '----------------------------------
111     CALL CLEARBOT(19, 5)
112     RFN$ = LEFT$(INN$(1), INSTR(INN$(1), ".") - 1)
113     AOK = 0: PFTH = 0: PFTL = 0
114     PFN$ = RFN$ + ".P" + CHR$(48 + PFTH) + CHR$(48 + PFTL)
115     CLOSE #1
116     OPEN "I", #1, PFN$
117     IF AOK = 1 THEN GOTO 118
            '------------------------ FILE EXISTS, HUNT FOR A FREE NAME
            CLOSE #1
            IF PFTH = 9 AND PFTL = 9 THEN PRINT "JACKPOT --- "; RFN$; ".PXX is full!": END
            IF PFTL = 9 THEN PFTH = PFTH + 1: PFTL = -1
            PFTL = PFTL + 1
            GOTO 114
            '-------------------------- FILE CLEAR, OPEN IT FOR DATA
118     CLOSE #1
119     OPEN PFN$ FOR OUTPUT AS #1
INITPL: '---------------------------- INITILIZE PLOTTER
            POUT$ = ESC$ + ".R": PLOTDATA (POUT$)      ' RESET PLOTTER
            POUT$ = ESC$ + ".Y": PLOTDATA (POUT$)      ' PLOTTER PROGRAMMED ON
            POUT$ = ESC$ + ".E": PLOTDATA (POUT$)      ' RESET ERROR LIGHT
```

A-20

```
            POUT$ = ESC$ + ".J": PLOTDATA (POUT$)        ' ABORTS PARTIAL CONTROL CODES
            POUT$ = ESC$ + ".K": PLOTDATA (POUT$)        ' ABORTS PARTIAL GRAPHICS CODES
            POUT$ = "IN;": PLOTDATA (POUT$)              ' INITIALIZE
            POUT$ = ESC$ + ".I127;;17;:": PLOTDATA (POUT$)' SET HANDSHAKE MODE 2
            POUT$ = ESC$ + ".N1;19:": PLOTDATA (POUT$)   ' SET EXTENDED HANDSHAKE MODE
            POUT$ = "IP0,0,10300,7650": PLOTDATA (POUT$) ' SET SCALE POINTS TO MAX
            POUT$ = "DI1,0;": PLOTDATA(POUT$)            ' INSURE TEXT ON X AXIS"
            POUT$ = "SI.14,.21": PLOTDATA (POUT$)        ' SET TEXT SIZE
            POUT$ = "TL;": PLOTDATA (POUT$)              ' TICK LENGTH
END SUB

SUB PLOTDATA (POUT$)
        ON ERROR GOTO ETRAP
        ON TIMER(30) GOSUB TTRAP: TIMER OFF
        ABORT = 0
        '--------------------- ABORT?????????
        QQ$ = INKEY$
        IF LEN(QQ$) = 1 THEN
          IF ASC(QQ$) = 27 THEN
            BEEP
            CALL CLEARBOT(20, 4)
            PRINT "You have pressed the <ESC> key."
            PRINT
            INPUT "Do you wish to abort?"; QQ$
            IF QQ$ = "y" OR QQ$ = "Y" THEN
              CLS
              COLOR 1, 4
              LOCATE 12, 27
              PRINT "Transmitting ABORT sequence!"
              POUT$ = ESC$ + ".R;PU;WPA0,0SP;"
              FOR STALL = 1 TO 7500: NEXT STALL
              ABORT = 1
            END IF
          END IF
        END IF
        '--------------------------- PUSH DATA TO PLOTTER
        IF VAL(INN$(3)) = 3 THEN PRINT #1, POUT$; : GOTO PDONE

TIMER ON
        XOFF$ = CHR$(19): XON$ = CHR$(17)

FOR XP = 1 TO LEN(POUT$)
          C$ = MID$(POUT$, XP, 1)
          WHILE (NOT EOF(1))
            CHK$ = INPUT$(1, #1)
            IF CHK$ = XOFF$ THEN FLGOFF = 1
            IF CHK$ = XON$ THEN FLGOFF = 0
          WEND
          WHILE (FLGOFF)
            CHK$ = INPUT$(1, #1)
            IF CHK$ = XON$ THEN FLGOFF = 0
          WEND
          PRINT #1, C$;
          FOR ZA = 1 TO 20: NEXT ZA
        NEXT XP

TIMER OFF
PDONE:  IF ABORT = 1 AND VAL(INN$(3)) = 3 THEN CLOSE #1: KILL PFN$
        IF ABORT = 1 THEN CLOSE #1, #2, #3: END
END SUB
```

```
        SUB PLOTDEMO
            ON ERROR GOTO ETRAP
8140    '------------------------------- PLOT PATIENT DEMOGRAPHOCS
        '------------------------------- WRITE WITH BLACK PEN
            POUT$ = "IWPUSP1DI1,0PA0,7550LB": PLOTDATA (POUT$)
            POUT$ = "Patient File :" + CRLF$: PLOTDATA (POUT$)
            POUT$ = "Name       :" + CRLF$: PLOTDATA (POUT$)
            POUT$ = "ID         :" + CRLF$: PLOTDATA (POUT$)
            POUT$ = "           " + CRLF$: PLOTDATA (POUT$)
            POUT$ = "Signal Averaged    Cycles" + CHR$(3): PLOTDATA (POUT$)
            POUT$ = "PA3000,7550LB": PLOTDATA (POUT$)
        '------------------
            POUT$ = "    " + CRLF$: PLOTDATA (POUT$)
            POUT$ = "Date :" + CRLF$: PLOTDATA (POUT$)
            POUT$ = "Time :" + CRLF$: PLOTDATA (POUT$)
            POUT$ = "    " + CRLF$: PLOTDATA (POUT$)
            POUT$ = "    " + CHR$(3): PLOTDATA (POUT$)
            POUT$ = "PA4500,7550LB": PLOTDATA (POUT$)
        '------------------
            POUT$ = "Age    :" + CRLF$: PLOTDATA (POUT$)
            POUT$ = "Gender :" + CRLF$: PLOTDATA (POUT$)
            POUT$ = "Height :" + CRLF$: PLOTDATA (POUT$)
            POUT$ = "Weight :" + CRLF$: PLOTDATA (POUT$)
            POUT$ = "Race   :" + CHR$(3): PLOTDATA (POUT$)
            POUT$ = "PA6300,7550LB": PLOTDATA (POUT$)
        '------------------
            POUT$ = "Medication 1 :" + CRLF$: PLOTDATA (POUT$)
            POUT$ = "Medication 2 :" + CRLF$: PLOTDATA (POUT$)
            POUT$ = "Systolic BP  :" + CRLF$: PLOTDATA (POUT$)
            POUT$ = "Diastolic BP :" + CRLF$: PLOTDATA (POUT$)
            POUT$ = "Option       :" + CHR$(3): PLOTDATA (POUT$)
            POUT$ = "PA8100,7050LB": PLOTDATA (POUT$)
        '------------------
            POUT$ = "Plot Time :" + CRLF$: PLOTDATA (POUT$)
            POUT$ = "Plot Date :" + CHR$(3): PLOTDATA (POUT$)
        '------------------------------ WRITE WITH RED PEN
            POUT$ = "SP2PA1200,7550LB": PLOTDATA (POUT$)
            POUT$ = IFILE$ + CRLF$: PLOTDATA (POUT$)
            POUT$ = SNA$ + CRLF$: PLOTDATA (POUT$)
            POUT$ = SID$ + CRLF$: PLOTDATA (POUT$)
            POUT$ = CRLF$: PLOTDATA (POUT$)
            POUT$ = " " + SC$ + CHR$(3): PLOTDATA (POUT$)
        '------------------
            POUT$ = "SI.21,.32PA2250,8900LB": PLOTDATA (POUT$) 'BIG SIZE TEXT
            POUT$ = "ACCELERATION FFT" + CHR$(3): PLOTDATA (POUT$)      'PROGRAM TITLE"
            POUT$ = "SI.14,.21": PLOTDATA (POUT$)          'NORM SIZE TEXT
            POUT$ = "PA3550,7550LB": PLOTDATA (POUT$)
        '------------------
            POUT$ = CRLF$: PLOTDATA (POUT$)
            POUT$ = SDA$ + CRLF$: PLOTDATA (POUT$)
            POUT$ = STI$ + CRLF$: PLOTDATA (POUT$)
            POUT$ = CRLF$: PLOTDATA (POUT$)
            POUT$ = CHR$(3): PLOTDATA (POUT$)
            POUT$ = "PA5250,7550LB": PLOTDATA (POUT$)
        '------------------
            POUT$ = SAG$ + CRLF$: PLOTDATA (POUT$)
            POUT$ = SEX$ + CRLF$: PLOTDATA (POUT$)
            POUT$ = SHT$ + CRLF$: PLOTDATA (POUT$)
            POUT$ = SWT$ + CRLF$: PLOTDATA (POUT$)
            POUT$ = SRA$ + CHR$(3): PLOTDATA (POUT$)
            POUT$ = "PA7500,7550LB": PLOTDATA (POUT$)
        '------------------
            POUT$ = SM1$ + CRLF$: PLOTDATA (POUT$)
            POUT$ = SM2$ + CRLF$: PLOTDATA (POUT$)
            POUT$ = SSBP$ + CRLF$: PLOTDATA (POUT$)
            POUT$ = SDBP$ + CRLF$: PLOTDATA (POUT$)
```

```
        POUT$ = SOP$ + CHR$(3): PLOTDATA (POUT$)
        POUT$ = "PA9035,7050LB": PLOTDATA (POUT$)
        '----------------
        POUT$ = TIME$ + CRLF$: PLOTDATA (POUT$)
        POUT$ = DATE$ + CHR$(3): PLOTDATA (POUT$)
END SUB

SUB RAWDRAW
        ON ERROR GOTO ETRAP
        CLS
        VIEW (0, 0)-(630, 238), 0, 0
        'LINE (0, 0)-(629, 0), 15
        'LINE (0, 0)-(0, 236), 15
        'LINE (0, 237)-(629, 237), 15
        'LINE (629, 0)-(629, 237), 15
        FOR PT = 0 TO 798
        LINE (PT / 1.27, (-XYZ(PT * 3) / 500) + 40)-((PT + 1) / 1.27, (-XYZ((PT + 1) * 3) / 500) + 40), 12
        LINE (PT / 1.27, (-XYZ(PT * 3 + 1) / 500) + 120)-((PT + 1) / 1.27, (-XYZ((PT + 1) * 3 + 1) / 500) + 120), 11
        LINE (PT / 1.27, (-XYZ(PT * 3 + 2) / 500) + 200)-((PT + 1) / 1.27, (-XYZ((PT + 1) * 3 + 2) / 500) + 200), 14
        NEXT PT

FOR PT = 79 TO 640 STEP 79
        LINE (PT, 0)-(PT, 240), 7, , &H8080
        NEXT PT

COLOR 9, 0: LOCATE 18, 1
        PRINT "0mS   100mS   200mS   300mS   400mS   500mS   600mS   700mS   800"

LINE (QRSON / 1.27, 0)-(QRSON / 1.27, 240), 14, , &H8080
        LINE (QRSOFF / 1.27, 0)-(QRSOFF / 1.27, 240), 14, , &H8080

COLOR 15, 0
        LOCATE 1, 1
        PRINT PROG$

COLOR 14, 0
        LOCATE 1, QRSON / 10.5: PRINT "QON"
        LOCATE 1, QRSOFF / 10.5: PRINT "QOFF"

LINE (BW / 1.27, 0)-(BW / 1.27, 240), 10, , &H7F7F
        LINE (EW / 1.27, 0)-(EW / 1.27, 240), 4, , &H7F7F
        COLOR 15, 0
END SUB
```

```
SUB SELWIND
        ON ERROR GOTO ETRAP
        POKE &H417, &H0 '------------ Clear shift lock
        BWEW = 0
        COLOR 15, 0
        '------------------------------------- ONE TIME PRINTING
        RAWDRAW
        CALL CLEARBOT(19, 5)

LOCATE 19, 1: COLOR 10, 0: PRINT "START:"
        LOCATE 19, 8: COLOR 15, 0: PRINT BW; "mS"

LOCATE 19, 24: COLOR 12, 0: PRINT "END:"
        LOCATE 19, 28: COLOR 15, 0: PRINT EW; "mS"

LOCATE 19, 44: COLOR 14, 0: PRINT "DELTA:"
        LOCATE 19, 51: COLOR 15, 0: PRINT EW - BW; "mS"

IF PROG$ = "FFT" THEN
          IF WIN = 0 THEN FRWF = .4
          IF WIN = 1 THEN FRWF = .7
          IF WIN = 2 THEN FRWF = 1
          LOCATE 19, 61: COLOR 14, 0
          PRINT "Freq. Res."
          LOCATE 19, 71: COLOR 15, 0
          PRINT FIX(10240 / ((EW - BW) * FRWF)) / 10; "Hz"
        END IF COLOR 7, 0
        PRINT "Keys:       <--,  -->,   End,   PgDwn,   F1"
        COLOR 15, 0
        PRINT "Functions:  -1mS,  1mS,  -10mS,  10mS,  Toggle Beg/End"

COLOR 14, 0: PRINT "Presets: ";
        COLOR 11, 0: PRINT "Intra-QRS"; : COLOR 14, 0: PRINT "<1> ";
        COLOR 11, 0: PRINT "Wide-QRS"; : COLOR 14, 0: PRINT "<2> ";
        COLOR 11, 0: PRINT "P-Wave"; : COLOR 14, 0: PRINT "<3> ";
        COLOR 11, 0: PRINT "P-R"; : COLOR 14, 0: PRINT "<4> ";
        COLOR 11, 0: PRINT "S-T(LP)"; : COLOR 14, 0: PRINT "<5> ";
        COLOR 11, 0: PRINT "-20/+100 Qoff"; : COLOR 14, 0: PRINT "<6>"
        LOCATE 23, 25: COLOR 14, 0: PRINT "<ENTER>"
        LOCATE 23, 33: COLOR 15, 0: PRINT "to accept values."

LOOPA:  '--------------------------- Loop point
        '--------------------------- MAKE CURSORS
        LINE (BW / 1.27, 0)-(BW / 1.27, 240), 10, , &H7F7F
        IF PROG$ = "FFT" THEN
          LINE ((BW + ((EW - BW) / 2)) / 1.27, 0)-((BW + ((EW - BW) / 2)) / 1.27, 240), 7, , &H7F7F
        END IF
        LINE (EW / 1.27, 0)-(EW / 1.27, 240), 4, , &H7F7F LOOPB:  QQ = XKEY '------------- WAIT FOR A KEY
        IF QQ = 13 THEN GOTO SDONE
        IF QQ = 3 OR QQ = 27 THEN CLOSE #1, #2, #3: END
        '--------------------------- BLANK CURSORS
        LINE (BW / 1.27, 0)-(BW / 1.27, 240), 0, , &H7F7F
        IF PROG$ = "FFT" THEN
          LINE ((BW + ((EW - BW) / 2)) / 1.27, 0)-((BW + ((EW - BW) / 2)) / 1.27, 240), 0, , &H7F7F
        END IF
        LINE (EW / 1.27, 0)-(EW / 1.27, 240), 0, , &H7F7F
        '--------------------------- REBUILD TRACES
        LINE (BW / 1.27, (-XYZ(BW * 3) / 500) + 40)-((BW + 1) / 1.27, (-XYZ((BW + 1) * 3) / 500) + 40), 12
        LINE (BW / 1.27, (-XYZ(BW * 3 + 1) / 500) + 120)-((BW + 1) / 1.27, (-XYZ((BW + 1) * 3 + 1) / 500) + 120), 11
        LINE (BW / 1.27, (-XYZ(BW * 3 + 2) / 500) + 200)-((BW + 1) / 1.27, (-XYZ((BW + 1) * 3 + 2) / 500) + 200), 10
```

```
IF PROG$ = "FFT" THEN
  MW = FIX((EW - BW) / 2) + BW
  LINE (MW / 1.27, (-XYZ(MW * 3) / 500) + 40)-((MW + 1) / 1.27, (-XYZ((MW + 1) * 3) / 500) + 40), 12
  LINE (MW / 1.27, (-XYZ(MW * 3 + 1) / 500) + 120)-((MW + 1) / 1.27, (-XYZ((MW + 1) * 3 + 1) / 500) +
  120), 11
  LINE (MW / 1.27, (-XYZ(MW * 3 + 2) / 500) + 200)-((MW + 1) / 1.27, (-XYZ((MW + 1) * 3 + 2) / 500) +
  200), 10
END IF
LINE (EW / 1.27, (-XYZ(EW * 3) / 500) + 40)-((EW + 1) / 1.27, (-XYZ((EW + 1) * 3) / 500) + 40), 12
LINE (EW / 1.27, (-XYZ(EW * 3 + 1) / 500) + 120)-((EW + 1) / 1.27, (-XYZ((EW + 1) * 3 + 1) / 500) +
120), 11
LINE (EW / 1.27, (-XYZ(EW * 3 + 2) / 500) + 200)-((EW + 1) / 1.27, (-XYZ((EW + 1) * 3 + 2) / 500) +
200), 10
'-------------------------- CAPTURE KEY
  IF QQ = 75 + 256 AND BWEW = 0 THEN BW = BW - 1
  IF QQ = 77 + 256 AND BWEW = 0 THEN BW = BW + 1
  IF QQ = 79 + 256 AND BWEW = 0 THEN BW = BW - 10
  IF QQ = 81 + 256 AND BWEW = 0 THEN BW = BW + 10
  IF QQ = 75 + 256 AND BWEW = 1 THEN EW = EW - 1
  IF QQ = 77 + 256 AND BWEW = 1 THEN EW = EW + 1
  IF QQ = 79 + 256 AND BWEW = 1 THEN EW = EW - 10
  IF QQ = 81 + 256 AND BWEW = 1 THEN EW = EW + 10

IF QQ = ASC("1") THEN BW = QRSOFF - 150: EW = QRSOFF + 150   'Intra-QRS
  IF QQ = ASC("2") THEN BW = QRSOFF - 170: EW = QRSOFF + 170   'Wide-QRS
  IF QQ = ASC("3") THEN BW = 150: EW = QRSON         'P-Wave
  IF QQ = ASC("4") THEN BW = 150: EW = QRSOFF        'P-R
  IF QQ = ASC("5") THEN BW = QRSOFF - 20: EW = 510   'LP
  IF QQ = ASC("6") THEN BW = QRSOFF - 20: EW = QRSOFF + 100
  IF QQ = 59 + 256 THEN IF BWEW = 0 THEN BWEW = 1 ELSE BWEW = 0
'-------------------------- CHECK CURSOR POSSITION
  IF BW > EW AND BW > BWOLD THEN EW = BW
  IF BW > EW AND EW < EWOLD THEN BW = EW
  BWOLD = BW: EWOLD = EW
  IF BW < 0 THEN BW = 0
  IF EW < 0 THEN EW = 0
  IF BW > 798 THEN BW = 798
  IF EW > 798 THEN EW = 798
'-------------------------- PRINT CHANGES
LOCATE 19, 8: COLOR 15, 0: PRINT BW; "mS "

LOCATE 19, 28: COLOR 15, 0: PRINT EW; "mS "

LOCATE 19, 51: COLOR 15, 0: PRINT EW - BW; "mS "

IF PROG$ = "FFT" THEN
  LOCATE 19, 71: COLOR 15, 0
  PRINT FIX(10240 / ((EW - BW) * FRWF)) / 10; "Hz "
END IF
'-------------------------- DO IT AGAIN
GOTO LOOPA
SDONE: '-------------------------- EXIT
  DELTA = EW - BW
END SUB
```

```
SUB SHOWDATA
        ON ERROR GOTO ETRAP
        '------------------------------ SHOW DATA ON THE SCREEN
        COLOR 11, 1
        PRINT
        PRINT "Bedside Recording made at "; STI$; " on "; SDA$
        PRINT "Unit # "; STU$; "   Site # "; STS$; "   1200EPX Software Version "; SSW1$
        PRINT '    TAB(60); ECGCK; SEQ
        COLOR 14, 1
        PRINT "PATIENT DATA:"
        PRINT
        PRINT "Patient Name : "; SNA$; "   Patient ID # : "; SID$
        PRINT "The Signal Average contains "; SC$; " accepted complexes."
        PRINT "Age "; SAG$; "   Gender "; SEX$; "   Height "; SHT$; "   Weight "; SWT$
        PRINT "Race "; SRA$; "   Medication 1 "; SM1$; "   Medication 2 "; SM2$
        PRINT "Systolic BP "; SSBP$; "   Diastolic BP "; SDBP$; "   Option "; SOP$
        PRINT
        PRINT "QRS onset at "; QRSON; "mS    QRS offset at "; QRSOFF; "mS"
        PRINT
END SUB FUNCTION XKEY
        ON ERROR GOTO ETRAP
KWAIT:  QQ$ = INKEY$: IF LEN(QQ$) = 0 THEN GOTO KWAIT
        IF LEN(QQ$) = 1 THEN
           IF ASC(QQ$) = 3 THEN CLOSE #1, #2, #3: END '---- CTRL C
           IF ASC(QQ$) = 27 THEN CLOSE #1, #2, #3: END '---- ESC
           XKEY = ASC(QQ$)
           EXIT FUNCTION
        END IF
        IF LEN(QQ$) = 2 AND ASC(LEFT$(QQ$, 1)) = 0 THEN
           XKEY = ASC(RIGHT$(QQ$, 1)) + 256
        END IF
END FUNCTION
```

What is claimed is:

1. A method for detecting micropotentials to identify cardiac arrhythmia comprising the steps of:

selecting a segment of interest of an electrocardiographic signal of one cardiac cycle;

generating a profile waveform representative of a temporal attribute of said segment of interest;

deriving a frequency domain spectral representation of said profile waveform, said frequency domain representation being representative of said segment of interest with high frequency micropotentials being amplified therein;

defining a bandwidth of interest of frequencies in said spectral representation;

determining a gradient from said spectral representation for each of a plurality of the frequencies within said bandwidth of interest;

obtaining a representative maximum amplitude of said spectral representation for the frequencies within said bandwidth of interest;

comparing said representative maximum amplitude and said gradients from said spectral representation for each of the plurality of the frequencies to detect the micropotentials in the segment of interest of the electrocardiographic signal; and quantifying a degree of spectral fragmentation within said bandwidth of interest from said comparing of said representative maximum amplitude and said gradients to identify cardiac arrhythmia.

2. A method in accordance with claim 1 wherein said selecting step comprises signal averaging of a plurality of cardiac cycles to reduce the noise level in a representative waveform.

3. A method in accordance with claim 2 wherein said generating step further comprises a step of taking a second derivative of said segment of interest of the electrocardiographic signal as said profile waveform representative of the temporal attribute.

4. A method in accordance with claim 3 wherein said deriving step further comprises the step of windowing said profile waveform in performing a frequency domain transformation using a Fourier transform.

5. A method in accordance with claim 4 wherein said defining step defines said bandwidth of interest as being about 50 Hz to about 300 Hz.

6. A method in accordance with claim 4 wherein said determining step comprises determining a gradient from said spectral representations for each of a plurality of the frequencies within said bandwidth of interest.

7. A method in accordance with claim 4 wherein said determining step comprises summing the absolute value of said gradients of said spectral representation within said bandwidth of interest.

8. A method in accordance with claim 4 wherein said obtaining step comprises identifying a plurality of spectral peaks from said spectral representation for the frequencies within said bandwidth of interest and discerning said representative maximum amplitude of said spectral representation as being the largest spectral peak identified.

9. A method in accordance with claim 7 wherein said comparing step comprises dividing the sum, determined in said determining step of summing the absolute value of said gradients of said spectral representation, by said representative maximum amplitude to compute an index quantifying the degree of spectral fragmentation within said bandwidth of interest.

10. A method for detecting micropotentials to identify cardiac arrhythmia comprising the steps of:

selecting a segment of interest of an electrocardiographic signal of one cardiac cycle;

generating a profile waveform representative of a temporal attribute of said segment of interest;

deriving a frequency domain spectral representation of said profile waveform, said frequency domain representation being representative of said segment of interest with high frequency micropotentials being amplified therein;

defining a bandwidth of interest of frequencies in said spectral representation;

characterizing a degree of variation within said bandwidth of interest of frequencies in said spectral representation to detect the micropotentials in the segment of interest of the electrocardiographic signal; and said characterizing step quantifying a degree of spectral fragmentation within said bandwidth of interest to identify cardiac arrhythmia.

11. A method in accordance with claim 10 wherein said generating step further comprises a step of taking a second derivative of said segment of interest of the electrocardiographic signal as said profile waveform representative of the temporal attribute.

12. A method in accordance with claim 11 wherein said characterizing step counts said spectral peaks to detect the micropotentials included in the frequency domain from about 50 Hz to about 300 Hz in the electrocardiographic signal to quantify the degree of spectral fragmentation therein.

13. A method in accordance with claim 10 wherein said characterizing step comprises the steps of:

identifying a plurality of spectral peaks from said spectral representation for the frequencies within said bandwidth of interest; and counting said spectral peaks to detect the micropotentials in the segment of interest of the electrocardiographic signal to quantify the degree of spectral fragmentation within said bandwidth of interest.

14. A method in accordance with claim 13 wherein said defining step defines said bandwidth of interest as being about 50 Hz to about 300 Hz.

15. An apparatus for detecting micropotentials to identify cardiac arrhythmia comprising:

a computer;

a signal storage device addressable by said computer;

a signal acquisition module operable with said computer to select a segment of interest of an electrocardiographic signal of one cardiac cycle, to save said segment of interest in said signal storage device and to generate a profile waveform representative of a temporal attribute of said segment of interest;

a frequency domain transformation program utilized by said computer to derive a spectral representation of said profile waveform representative of said segment of interest with high frequency micropotentials being amplified within a bandwidth of interest for characterizing a degree of variation within said spectral representation to detect the micropotentials in said segment of interest of the electrocardiographic signal; and said frequency domain transformation program quantifying a degree of spectral fragmentation within said bandwidth of interest to identify cardiac arrhythmia.

16. An apparatus in accordance with claim 15 wherein said frequency domain transformation program utilized by said computer comprises:

means for determining a gradient from said spectral representation for each of a plurality of the frequencies within said bandwidth of interest;

means for obtaining a representative maximum amplitude of said spectral representation for the frequencies within said bandwidth of interest; and means for comparing said representative maximum amplitude and said gradients from said spectral representation for each of the plurality of the frequencies to detect the micropotentials in the segment of interest of the electrocardiographic signal to quantify the degree of spectral fragmentation within said bandwidth of interest.

17. An apparatus in accordance with claim 15 wherein said signal acquisition module operable with said computer comprises means for taking the second derivative of said segment of interest of the electrocardiographic signal as said profile waveform representative of the temporal attribute.

18. An apparatus in accordance with claim 16 wherein said comparing means comprises means for determining the absolute value of said gradients of said spectral representation, and summing said absolute value of said gradients within said bandwidth of interest, and dividing the sum of the absolute value of said gradients of said spectral representation by said representative maximum amplitude to compute an index quantifying the degree of spectral fragmentation within said bandwidth of interest.

19. An apparatus in accordance with claim 15 wherein said frequency domain transformation program utilized by said computer comprises means for characterizing the degree of variation within said bandwidth of interest of frequencies in said spectral representation to detect the micropotentials in the segment of interest of the electrocardiographic signal to quantify the degree of spectral fragmentation within said bandwidth of interest.

20. An apparatus in accordance with claim 19 wherein said means for characterizing comprises:

means for identifying a plurality of spectral peaks from said spectral representation for the frequencies within said bandwidth of interest; and means for counting said spectral peaks to detect the micropotentials in the segment of interest of the electrocardiographic signal to quantify the degree of spectral fragmentation within said bandwidth of interest.

21. A method for detecting micropotentials to identify cardiac arrhythmia comprising the steps of:

selecting a segment of interest of an electrocardiographic signal of one cardiac cycle;

generating a profile waveform representative of a temporal attribute of said segment of interest;

deriving a frequency domain spectral representation of said profile waveform, said frequency domain representation being representative of said segment of interest with high frequency micropotentials being amplified therein;

defining a bandwidth of interest of frequencies in said spectral representation;

determining a gradient from said spectral representation for each of a plurality of the frequencies within said bandwidth of interest;

obtaining a representative spectral change index for the frequencies within said bandwidth of interest;

comparing said representative spectral change index and said gradients from said spectral representation for each of the plurality of the frequencies to detect the micropotentials in the segment of interest of the electrocardiographic signal; and quantifying a degree of spectral fragmentation within said bandwidth of interest from said comparing of said representative spectral change index and said gradients to identify cardiac arrhythmia.

22. A method in accordance with claim 21 wherein said selecting step comprises signal averaging of a plurality of cardiac cycles to reduce the noise level in a representative waveform.

23. A method in accordance with claim 22 wherein said generating step further comprises a step of taking a second derivative of said segment of interest of the electrocardiographic signal as said profile waveform representative of the temporal attribute.

24. A method in accordance with claim 23 wherein said deriving step further comprises the step of windowing said profile waveform in performing a frequency domain transformation using a Fourier transform.

25. A method in accordance with claim 24 wherein said defining step defines said bandwidth of interest as being about 50 Hz to about 300 Hz.

26. A method in accordance with claim 24 wherein said determining step comprises determining a gradient from said spectral representations for each of a plurality of the frequencies within said bandwidth of interest.

27. A method in accordance with claim 24 wherein said determining step comprises summing the absolute value of said gradients of said spectral representation within said bandwidth of interest.

* * * * *